United States Patent [19]
Smith et al.

[11] Patent Number: 6,018,860
[45] Date of Patent: *Feb. 1, 2000

[54] PROCESS FOR MANUFACTURING DRILLED TAPER POINT SURGICAL NEEDLES

[75] Inventors: Daniel J. Smith, Manalapan Township, N.J.; Bernard M. Willis, Lawrenceville, Ga.; Paul K. Marschke, Bordentown, N.J.

[73] Assignee: Ethicon, Inc., Somerville, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/946,478

[22] Filed: Oct. 7, 1997

Related U.S. Application Data

[63] Continuation-in-part of application No. 08/665,054, Jun. 7, 1996, Pat. No. 5,701,656.

[51] Int. Cl.[7] .................................................. B23P 13/04
[52] U.S. Cl. ........................... 29/558; 29/33 F; 29/423; 29/559; 29/563; 451/130; 451/140; 451/184; 451/244; 83/35; 72/379.2

[58] Field of Search ................................ 29/7, 33 F, 56.5, 29/423, 557, 558, 559, 563, 564, 564.3, 564.6, 564.7; 451/48, 49, 54, 130, 140, 182, 184, 242, 244; 83/35, 40; 470/34–40

[56] References Cited

U.S. PATENT DOCUMENTS 5,539,973   7/1996   Smith et al. ............................ 29/558

*Primary Examiner*—David P. Bryant
*Attorney, Agent, or Firm*—Emil Richard Skula

[57] ABSTRACT

A process for manufacturing wire or needles having a taper point and mechanically drilled suture mounting holes in the proximal ends. Needle or wire blanks are cut from a roll of wire and mounted to a carrier strip. The carrier strip and needles are moved through a succession of forming and trimming and grinding stations. The blanks are coined in a coining die to produce lateral wings of constant thickness. The blanks are preferably rotated in the strip while being ground. The strip and needle blanks are then moved to a bank of at least two drills wherein the proximal suture mounting ends of the needles are drilled.

3 Claims, 28 Drawing Sheets

PROCESS FOR MANUFACTURING DRILLED TAPER POINT SURGICAL NEEDLES

This is a Continuation-In-Part Application of commonly assigned patent application Ser. No. 08/665,054 filed on Jun. 7, 1996.

TECHNICAL FIELD

The field to which this invention pertains is surgical needles, more specifically, a method of manufacturing taper point surgical needles, especially mechanically drilled needles.

BACKGROUND OF THE INVENTION

Surgical needles and methods of manufacturing surgical needles are well known in the art. Surgical needles typically consist of a shaft-like member, which may be curved or straight. The member has a distal piercing point and a proximal end for mounting or receiving a suture. Surgical needles are typically classified as either taper-point needles, wherein the diameter of the shaft tapers to a piercing pint, or cutting edge needles wherein the needles have various cutting edges along with piercing points to assist in penetrating various types of tissue.

Surgical sutures may be attached or mounted to the proximal ends of surgical needles in various ways. One common way is to have a channel formed into the proximal end of the needle. The channel end typically is die-formed into a needle during the manufacturing process and consists of a cavity. When a surgical suture end or tip is placed into the cavity, the channel end is hit with a die one or more times under pressure forcing the sidewalls closed tightly about the suture tip to prevent the suture from separating from the needle. The process of mounting a suture tip to the proximal end of a needle is known in the art as swaging. Another manner in which a suture may be mounted to a surgical needle is by drilling a hole, commonly referred to in the art as blind hole, into the proximal end of the needles. This can be done using conventional mechanical drilling apparatuses or conventional laser drilling apparatuses. The end or tip of a suture is then inserted into the drilled hole and the section of the proximal end of the needle surrounding the blind hole is swaged in a conventional manner by compressing with various conventional dies. It is also known to mount suture to surgical needles using conventional adhesives.

Surgical needles are conventionally manufactured from surgical grade alloys, such as surgical grade stainless steel, which are purchases from manufacturers in the form of rod or wire. The rod is drawn into wire and rolled onto a spool. The initial step in the manufacture of surgical needles is to remove the wire from the spool, degrease or clean if required, and then cut the wire into sections known as needle blanks. Each blank will have a length greater than the length of the finished needle, since material will necessarily be removed from the blank during the needle manufacturing process.

A conventional process for manufacturing a taper point needle typically consists of cutting wire into needle blanks and taking each needle blank and subjecting the blank to a series of grinding operations. This is conventionally done in the following manner. The needles blanks are fed into a conventional belt/stone grinding machine where they are given a distal tip. The needles are then transported individually or in bulk to a conventional needle drilling station wherein the needles are drilled using conventional carbide or tool steel drill bits to provide a proximal suture mounting cavity. The needles are then typically degreased and moved in bulk to a conventional belt/stone grinding machine for the finish taper grind and then to a curving machine to produce a conventional curved configuration. The needles are then cleaned, heat treated and may be electrochemically treated to additionally finish the needles. The conventional process is a batch process requiring the handling of the needles in bulk containers to transport them to and from the various work stations. Needles may become damaged or intermingled during such bulk transfers. In addition, the needles must typically be individually mounted in chucks in each machine at each work station. Although this chuck mounting step may in some circumstances be automated, it is typically a time consuming, labor intensive operation.

One conventional method of manufacturing cutting edge needles consists of initially cutting wire into blanks as described above. The distal tips of the needle blanks are then rotary swaged in a rotary swaging machine to produce a conical point having a spud. The spud is next partially cut and the needle blanks are then moved to a belt/stone grinder and mounted into chucks wherein the distal tip of each needle blank is given the final grind to create the necessary shape for bayonet closed die forming. The needle blanks are then moved in bulk or by chuck to a die station where each needle blank is die-formed. The needle blanks are then subjected to a series of grinding operations in a conventional belt/stone grinding machine to produce the cutting edge shape, for example, eight or more separate grinds. The needle blanks must be removed from the chucks and remounted in chucks after and prior to each grinding step, typically by using a walking beam mechanism. The extensive bulk and manual handling required by this process may result in damage to the needles, including the dulling of the points. In addition, the needle machines used in the prior art processes are operator dependent. Each operator tends to set up a machine differently resulting in variability in needle geometry and performance characteristics. Since surgical needles are quality control tested prior to release, the problems associated with the prior art processes tend to result in a financial burden upon the manufacturer in that a significant amount of the needles produced may have to be rejected and destroyed.

The previously described processes are labor intensive and typically utilize low speed, low output equipment. The needles are typically manually handled and transferred in bulk containers between various work stations or machines. In addition, numerous grinding steps are usually required. Often, needles are damages, including the dulling of needle points, due to the extensive handling and numerous grinding steps which are present in these processes. It is known that grinding operations are by their very nature imprecise resulting in wide variations in the dimensions of the finished needles. This imprecision resultingly yields a significant degree of geometric variability.

The disadvantages of the previously-mentioned prior art processes has been overcome in part by a process in which needle blanks are mounted to a carrier strip and moved to a plurality of finishing steps. Such a process is disclosed in U.S. Pat. No. 5,477,604 which is incorporated by reference. In this type of process, a taper point surgical needle is manufactured by progressively forming a needle blank. The tooling and dies referred to in this patent have been used and known in the art. It is commonly known to those skilled in the art of high speed forming and stamping that such tools and dies are not used alone. These tools are typically contained in holders or modules. These die set modules can then be placed in conventional larger more robust holders commonly referred to as a die post or die set. These larger systems are then placed and fastened into a die press. The presses can be free standing or contained as one or many presses (5 ton, 10 ton, 50 ton, etc.). The reasons for doing this are many, and vary throughout different industries. For example, with surgical needles accuracy, placement and repeatability are amongst the top. A system such as described above also allows for quick tool changes and reduced setup times, which increase machine efficiencies. A combination of these die sets can be arranged to produce the desired surgical needle or part. Typical die sets can contain a few or hundreds of individual parts that are integral to each other, e.g., die stops are commonly used to regulate or control the motion of a press. Tools or dies can be sensed using conventional devices such as conventional load cells to indicate tool wear. Tooling, dies and presses as described herein can be commercially purchased, or seen at trade shows in a variety of uses. The process consists of the initial step of cutting needle blanks from a roll of wire and mounting the blanks in a carrier. The carrier is cut and formed from strip located near the machine. The carrier transports the blanks to a succession of work stations on two different machines. At the initial machine and work station, the needle blank is coined in at least one conventional closed die having a cavity. Each needle blank is then moved successively to a trim station where flash is trimmed from the needle blanks using a punch and die. Optionally, the needle blank can be transported to one or more additional coining and trimming stations. Then each needle blank is moved to a grinding station wherein the needle blank is rotated about its longitudinal axis in the carrier as the distal tip of the needle blank is ground with a high speed grinding wheel parallel to the longitudinal axis of the needle blank. Needles are flattened and spooled prior to being moved to a second machine. This happens after the second machine which locates, curves and drills the blank. Following the coining and trimming operations described above, the needle points are ground to the final desired shape on contoured grinding wheels. Prior art grinding wheels are comprised of two plated profiled grinding wheels. This arrangement could result in needle chatter which may cause premature failure of the wheel that rotates in the same direction as the needle blank.

An improved configuration has been developed. Grinding wheels have been prepared consisting of a single plated profiled grinding wheel in concert with a non-plated hardened wheel. The plated wheel is plated with an abrasive such as Borzon or diamond. The non-plated hardened wheel can be preferably contoured or angled. Hardening of this wheel is necessary to reduce galling, scratching and pick-up on the non-plated surface. It was unexpected that such an arrangement would reduce needle chatter but it has proven to successfully reduce costs, improve point quality and reduce set-up times.

The grinding systems described in the prior art may exhibit build-up of grinding debris on the contoured surfaces of the wheels and within the workings of the machine. This results in shortened grinding wheel life and inconsistent grinding and bent needle blanks. It is commonly known that chemical bonding is often encountered when high speed grinding stainless steel with Borzon or diamond grit wheels. To eliminate this problem, a custom drip oiler cleaning system and method has been developed. This vacuum oiler system and method consists of dripping oil on the top portion of the grinding wheels with the drip aligned along the central longitudinal axis of the wheels and just proximal to the location of contact of the needle blank with the contoured wheels and a vacuum system located just distal to the location of contact of the needle blank with the contoured wheels (see. FIG. 22). The preferred location of the vacuum source is as shown in FIG. 22. Other locations for the vacuum source have been found to be less efficient in maintaining the grinding wheel surfaces in a clean state. The entire system is enclosed within a housing to contain all fluids and debris.

The primary function of the vacuum oiler cleaning system is not lubrication. It is unlike lubricating systems, which are used for cooling in wet grinding systems in that conventional lubricating systems simply employ conventional lubricants under constant flow and without vacuum recovery.

This combination of plated wheels, grit size, oil drip, vacuum, and transverse grinding on center of the hub allows for accurate high speed formation of each needle blank over millions of parts. High speed grinding as describe for this system can optimally range between 25 ms–150 ms of actual grinding time to complete the tapered point. Typical wheel life in this system ranges between 750,000 and 3.5 million needles.

After needles are fully processed on the first machine they are spooled and prepared for loading on the second machine for the drilling operation. The nature of the drilling operation is unique and requires a combination of a small incremental de-spooling of carrier strip with a greater incremental in-feed to the drilling. This requires the system to have the standard strip "push" and a strip "pull". The strip is pushed or fed from the spool and looped in an arrangement to allow lengths of the strip to accumulate. The drilling machine intermittently "pulls" required lengths of the strip for drilling operations. In this embodiment, de-spooling increments are about 0.5" and the intermittent length of strip pulled is about 2". This is a function of the number of drills in the drilling bank and will vary accordingly. Typically, there are at least two drills in the drilling bank. The drill heads, in each drilling bank, are separated from each other by 4". The needle blank is then cleaned, heat treated, and electrochemically treated. The finished needle is optionally siliconized.

In a variation of this process, the surgical needles are mechanically drilled to form distal suture mounting holes while the needles are mounted to the carrier strip. After the points are formed, the strip and needles are transported to a second machine where the blank is repositioned, curved using one or more stations or moved to a banked drilling station. Prior to the drilling station, the carrier is modified by cutting out a section to allow drilling. Needle making requires many operations occurring at a series of manufacturing stations. Needles may be held and moved between stations by use of a carrier strip. Manufacturing operations are required at both the proximal and distal ends of the needle blanks. Prior art carrier strips only allow for such operations to occur at one end of needle blanks. This necessitates the needles be singulated and possibly reloaded onto a second carrier strip for subsequent processing. A special carrier strip has been developed which allows for needle operations to occur at both the proximal and distal ends of needle blanks. This multipurpose carrier strip reduces cost and maintains constant control of the needle blank. This strip further includes access ports for removing a proximal portion of the needle tail upon completion of processing of the distal end of the needle blank. Once the proximal portion of the needle tail is removed, the needle blank is then repositioned and the back of the strip is trimmed away converting the strip so that subsequent needle hold drilling may be conducted on the proximal end of the needle.

The carrier strip includes two different tab designs. The first tab design is similar to those previously disclosed. The second tab design is unique in that it surrounds the distal portion of the needle tail and is subsequently formed around the distal portion of the needle tail and snapped back into the slot from which it was originally punched. This securely holds the needle in place. The second tab design is first pre-punched with very small holes at the stress points and subsequently cut to eliminate unwanted deformation of the strip. Any repetitive deformation of the strip will cause the strip to bow or camber. For example, a 0.0001" deformation associated with each second tab formation will result in a camber of 0.5" or greater over 5 to 6 feet. Deformation of this nature is unwanted in that it will result in needle twisting and jamming in subsequent operations. Where deformations of this nature are not preventable, off-setting deformations may be purposely made at other periodic locations along the carrier strip.

The multipurpose carrier strip of this process is used to process needles on two machines. The first machine fabricates the distal end of the needle and the second machine forms a drilled hole in a proximal end of the needle. Utilizing two machines, as described in this prior art process, both needle making and drilling operations are optimized. Needle making operations include point and body formation (including needle curving). Spooled needles formed following the first machine are later fed off the spool into a second machine in the opposite direction. That is to say, the last needle processed on the first machine is the first needle to be processed on the second machine. When feeding needles from the multipurpose carrier strip into the drilling machine, it is preferred that curved needle points trail the direction of feed off the spool. This minimizes point damage as the strip is pulled through the drilling machine. It is possible to combine both proximal and distal needle operations into one machine. However, if combined together into one machine, set-up times, efficiencies, set-up east and operator visibility are expected to be compromised.

A welding system may be utilized along with a custom alignment device to accurately attach the end of one strip to the beginning of a new strip. It is important that the strip pilot progression, or registration not be altered more than about +/−0.0002" to assure proper positioning in high speed manufacturing equipment. Other methods of connecting the strips together are possible such as clips, or tape, etc.

The drilling stations in such a drilling process consist of a bank of four or more conventional mechanical drills having conventional helical cutting edges. The drilling operation utilizes a unique progressive linear (4 up) arrangement which differs from conventional bank drilling systems. Conventional bank drilling systems utilize a rotary table having a series of stations which progressively drill deeper and/or larger holes in parts held in chucks which are spaced in increments less than the diameter of individual drilling heads. With this invention, the spacing of needles on the strip is 0.5". To overcome this problem, we have developed a unique linear single depth drilling system. The layout of drilling heads, the strip progression and needle registration are all considered. The strip is advanced in an intermittent fashion, allowing for drilling four non-consecutive needles on the strip. The system uses two drilling banks of four drilling heads each and has the ability of additional backup drilling banks if desired. Each drilling bank is driven by two servo motors and four drill motors. Backup drilling banks allow for the machine to continue to run if there is a failure with any of the primary drilling banks. Automatic switch over to the backup drilling banks can occur allowing an operator to correct any undesirable situation with the primary drilling banks. Alternately, individual drill heads have been equipped with quick disconnect collets to facilitate drill changes within seconds. The use of these collets eliminated the need for an automated switching to back up drilling banks due to undesirable situations occurring with any of the primary drilling banks. The drills may be modified to have an offset (see FIG. 20) point providing for a drilled hole which is larger than the outside diameter of the drill. Initially, the needles are moved to a bank of drills which provide a centering hole in addition a micropunch can be used to further aid in centering of the micro drills, then moved to a second set of drills which drill the suture mounting hole to the desired depth. It is commonly known by those skilled in the art of hole drilling to use a starter hole to keep small drills from "walking" around when they start to drill. In the manufacture of surgical needles, a center drilled hole is used and a separate hole drill is used to drill a blind hole. The depth of blind holes in surgical needles are typically 4–6 times the diameter of the drill used. A primary purpose of the center drill with surgical needle manufacturing is to assist in feeding suture machine into the hole in preparation for subsequent needle/suture attachment operations. Additionally, these center drilled holes provide a smooth burr free surface necessary to prevent damage to the later attached suture material. Center drilling can take the form of center drill or the like. A center drill has a conical shape and a flat point. The hole produced by such a center drill leaves a conical shape with a flat bottom. The size of the center drill required to produce a contour for suture insertion and attachment is large. While this size center drilled hole may be adequate for many subsequent drilling operations (to prevent small drills from "walking"), it is inadequate when the subsequent operation calls for a drill, such as a micro drill, with a diameter less than the width of the flat bottom section in the center drilled hole. This is often the case with surgical needles where the subsequent small drill to be used is very small. Thus, the function of the center drill is defeated and the small drill "walks" around on the flat bottom of the center drilled hole. To overcome this problem we developed a system to centrally punch the bottom of the center drilled hole. This improvement allows the micro drill to start in the center until the hole is deep enough that the side of the drill contact the walls of the center drill cone. This is particularly beneficial on drills smaller than 0.015" in diameter. The drilled needles are then moved to an optional plug depth measuring station to detect improperly drilled holes.

A special oil separator and recycling system has been used in conjunction with a vacuum system to evacuate the drill chip and excess lubricant from the hole and tooling area. This is an extremely critical step to the described process. Prior art has described the use of oil and/or air in an attempt to remove drill chips and lubricant from the drill. The conventional method was improved by cycling the spray of oil so that it is on only when required for drilling. Running the system in this manner maximizes the amount of oil on the drill during drilling and minimized the amount of oil consumption.

When using the previously-mentioned drilling process with a conventional progressive forming process, the needles are preferably spooled prior to drilling or fed directly to the drilling apparatus. If spooled, the spooled needles are loaded into a de-coiling apparatus which feeds the carrier and needles by means of conventional mechanical grippers to the second machine which repositions curves and drills. Carrier strips may be spooled on cores for transport between machines. Core diameter should be large enough so curved needles are not damaged by subsequent wraps of needles, and so that the needles are not loosened up by bending the strip over a small radius. Small needle wire sizes typically use a core of about 9 inches in diameter and achieve a spool size of about 2.5 feet or greater. Large diameter needles may reach 4 feet in diameter on the same size core. The curving and drilling apparatus could have various functions to turn and orient the needles for the various operations. The needles and carrier are then moved to a conventional curving station or multiple stations (four or more) where the needles are curved while still mounted to the carrier. The needles have an extra ½" to allow the complete curving of the blank. In later steps this extra portion will be repositioned and cut off. Next, the blank is repositioned, the strip and tails of the needles are cut using the pre-punched holes in the carrier. The strip is pushed into the loop and pulled into the drilling machine, the drills used for drilling are modified. The drill tips are altered to lengthen one side creating an off set center point. This offsets the center of the drill and allows the drill to cut a slightly larger, yet accurate hole. This technique increased drill life from about 1,000 needles per drill to over 15,000 needles per drill (there have been some drills that have lasted in the 30K to 75K range before breaking). Prior to this discovery, such drill life numbers using conventional drill types were not thought possible in high speed deep hole drilling of stainless steel material, especially where hole depths range between 4 and 6 times drill diameter.

The needle blanks (either straight or curved) are rotatably mounted on the carrier strip. This allows for axial and rotational motion. A section of the carrier is cut off to allow drilling, and the needles and carrier are then moved into a loop take-up prior to entering the first drilling station, where a bank of four conventional mechanical drills is used to drill the proximal end of each of the four needles which are not adjacent to each other. Accurate carrier and positioning systems (+/-0.0001 or 0.0002 tenths) allow for good locationing of work pieces in automated equipment. One means for achieving this accuracy comes from progressive on-line stamping of a carrier strip. Once formed, the carrier strip can be piloted throughout the process, this allows the equipment to have a sufficient clearance to minimize jamming of the carrier strip while maintaining accurate placement at the tool. Prior to drilling, the needles may be positioned to assure maximal alignment. It is preferred that the needles be counter sunk prior to the initial drilling step. The suture mounting hole may be drilled in a succession of depths by successive banks of drills at successive drilling stations. In addition, a conventional plug type probe may be utilized at a test station to test the depth of each drill. Improperly drilled needles are identified and not removed. The good needles are then removed from the carrier and the carrier is typically cut into sections for scrap disposal. It is possible to leave the needle on a strip as a spool or to cut into individual strip segments for further processing (in which case one would remove the bad needles)

There is a continuing need in this art for improved progressive forming processes for manufacturing taper point needles.

DISCLOSURE OF THE INVENTION

Therefore, it is an object of the present invention to provide a novel progressive forming process for manufacturing taper point needles.

Accordingly, an improved process for manufacturing taper point surgical needles by progressively forming a needle blank is disclosed. In this process, a plurality of needle blanks having proximal and distal ends are rotatably mounted to a carrier strip, and each needle blank is moved to a first forming station wherein the distal tips are coined to form a point having lateral wings extending therefrom. The needle blanks are then trimmed to remove any excess wings prior to grinding. The needles and strip are then moved to a grinding station wherein the distal coined/trimmed tip of each needle blank is ground while the needle blank is rotated in the carrier to produce a surgical needle having a distal piercing tip, and the needles are then moved on the carrier to a flattening station wherein the body section of each surgical needle is formed. Next, the blank is repositioned curved and cut before a section of the carrier is cut away to allow drilling. The carrier and needles are then moved to at least one bank of mechanical drills wherein the proximal ends of at least four surgical needles are simultaneously drilled with mechanical drills, and then moved to at least one plug testing station wherein the depth of the holes in the needles is measured. Finally, the good needles are removed from the carrier strip. The improvement of the present invention consists of providing a coining die such that the lateral wings coined into the distal tip of each needle blank are of constant thickness.

Other features and advantages of the invention will become more apparent from the following description and accompanying drawings.

BEST MODE FOR CARRYING OUT THE INVENTION

Figure 1:
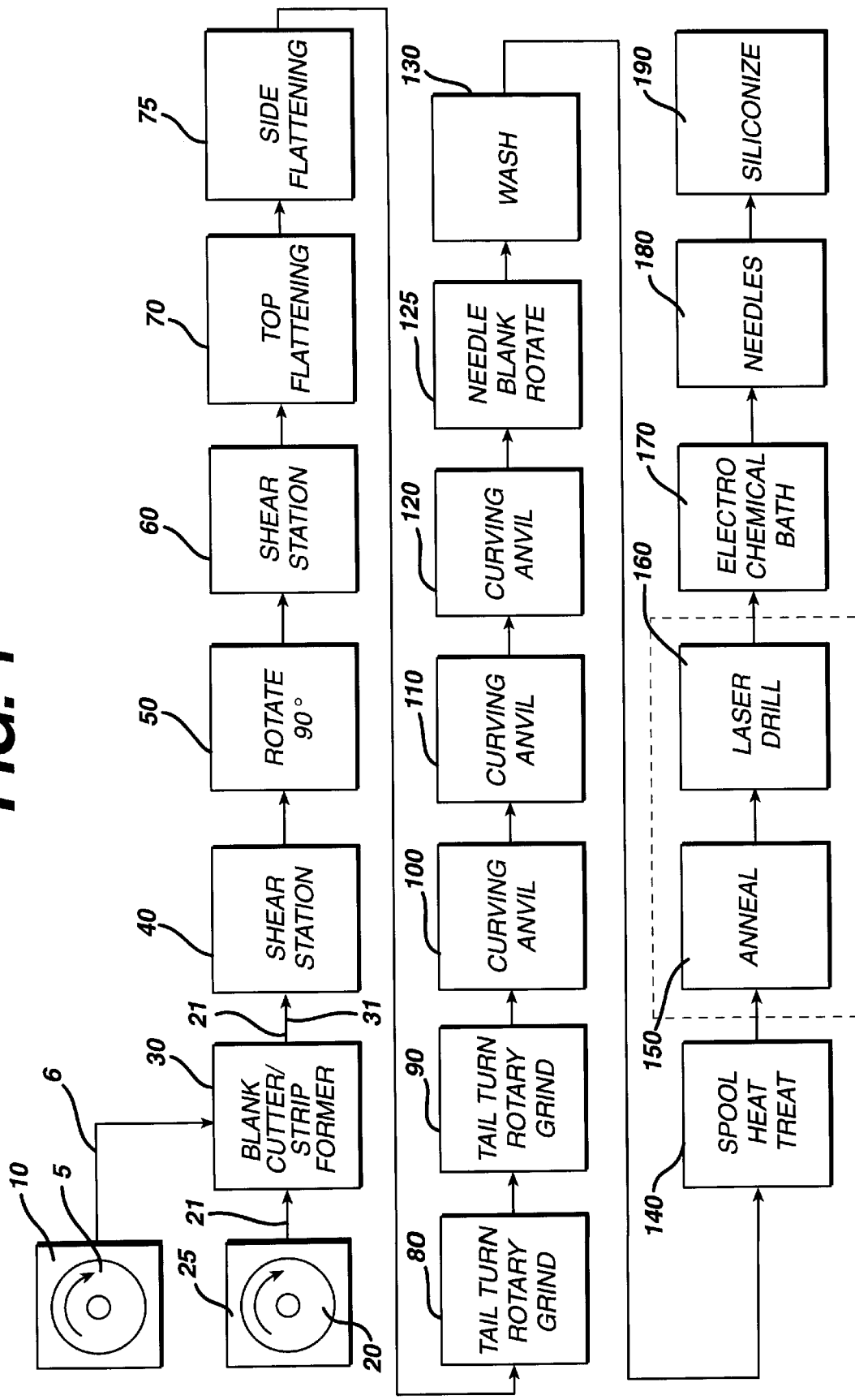
FIG. 1 is a flow diagram illustrating a process of the present invention wherein the distal end of the needle blank is trimmed prior to grinding.

Referring to FIG. 1, a flow diagram for a needle manufacturing process of the present invention is illustrated.

Figure 3:
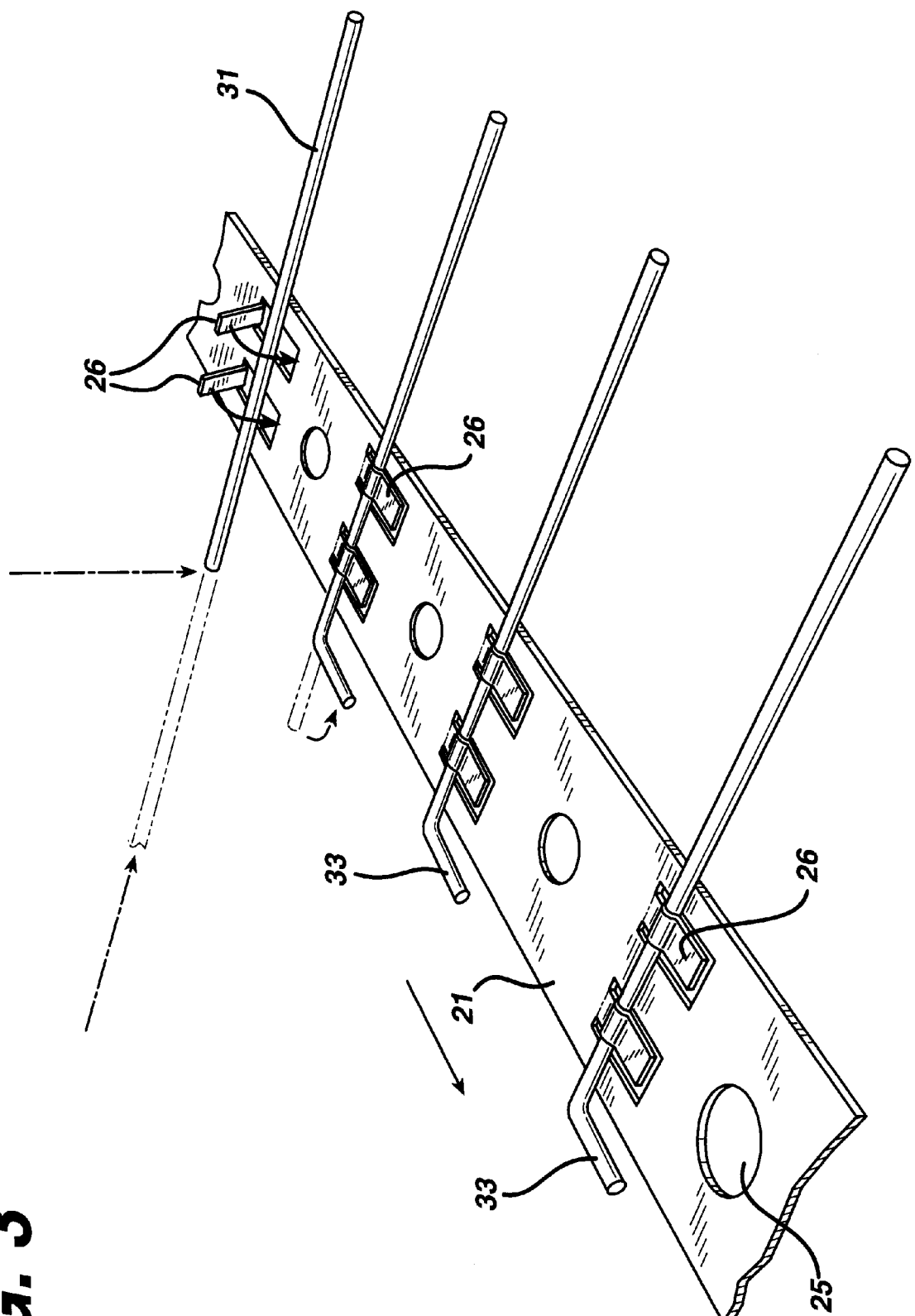
FIG. 3 is a perspective view of a needle blank after it has been cut by the blank cutter/strip former machine; the needle blank is seen mounted in a section of carrier strip with the proximal end or tail bent.
Figure 4:
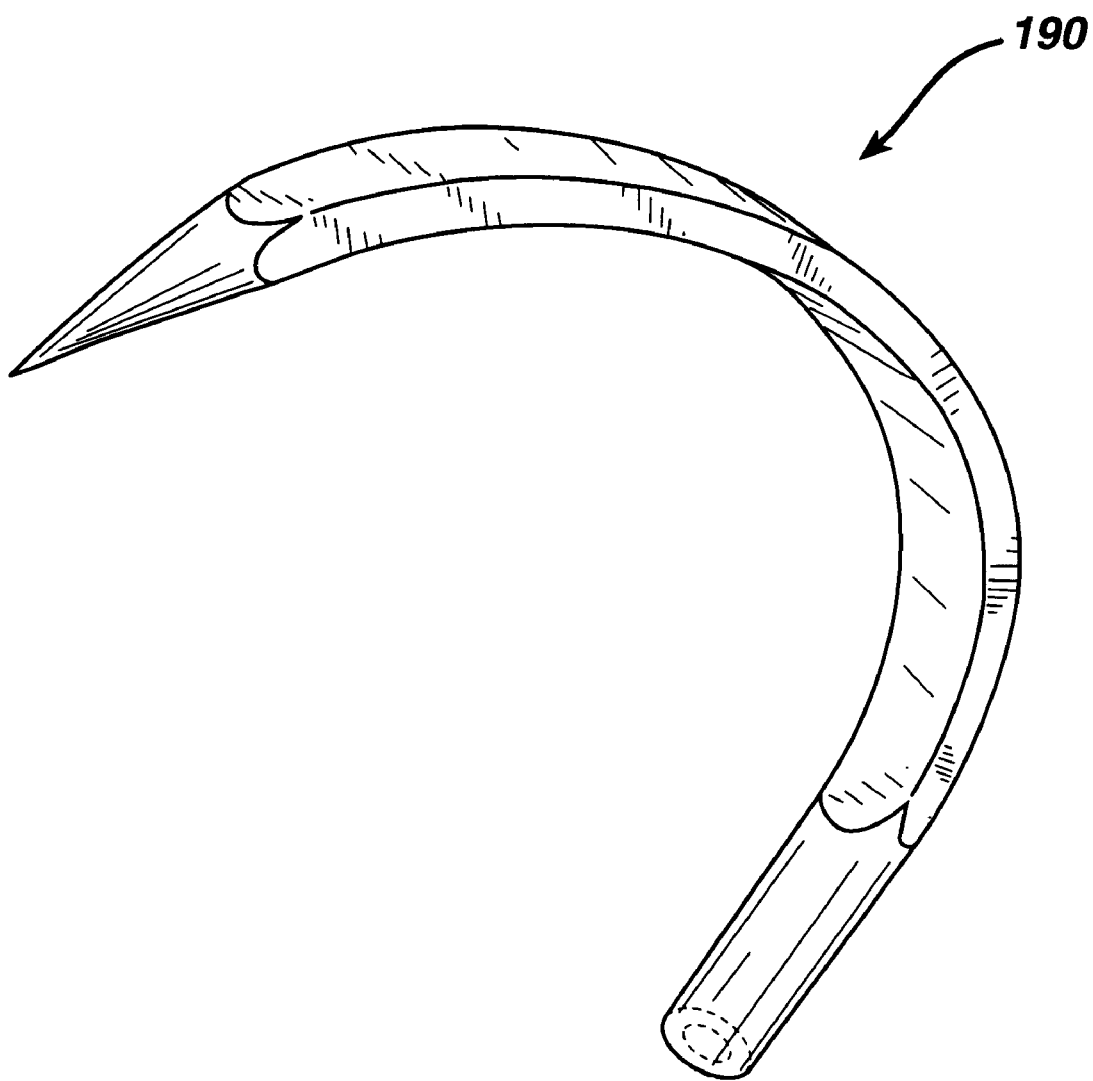
FIG. 4 is a perspective view of a taper point needle produced by the process of the present invention.

Initially wire 6 from roll 5 is fed by a conventional gripper/feeder machine 10 to blank cutter/carriage strip former machine 30. The roll 5 is rotatably mounted inn gripper/feeder 10. Simultaneously, the carrier strip 21 is fed from carrier strip roll 20, which is rotatably mounted in conventional gripper/feeder machine 25 to blank cutter/carriage strip former machine 30. In blank cutter/carrier strip former machine 30, the wire 6 which is fed from gripper/feeder 10 is cut into lengths which are conventionally referred to as needle blanks 31. As the needle blanks 31 are being cut, the blank cutter/carrier strip former 30 is simultaneously processing the carrier strip 21. The carrier strip 21 typically consists of a steel strip known as a bandoleer. The strip will be sufficiently thick sufficiently wide and sufficiently flexible to effectively move and retain needle blanks while being capable of being die punched and formed. Preferably the bandoleer is made of a flexible metal such as cold rolled steel and equivalents thereof. However, the bandoleer may also be made from polymeric materials such as engineered, reinforced polymers and equivalents thereof. The wire 6 being fed from gripper/feeder 10 is cut into lengths which are conventionally referred to as needle blanks 31 within blank cutter/carriage strip former machine 30. As the needle blanks 31 are being cut, the blank cutter/carrier strip 30 is simultaneously processing the carrier strip 21 in the following manner. Carrier strip 21 is processed to receive needle blanks 21 and to engage indexing controls within the various work stations. The carrier strip 21 is die cut, formed and crimped to produce a carrier strip having indexing pilot holes 25 and crimps which form mounting tabs 26 for receiving, engaging and holding needle blanks 31. A section of carrier strip 21 having needle blanks 31 mounted therein is seen in FIG. 3. Then, needle blanks 31 are cut and inserted into the mounting tabs 26 of carrier 21 by inserting the wire 6 into each tab 26 and then cutting the wire 6 to form a needle blank 31. The tabs are then crimped to retain the needle blanks 31. The proximal ends 32 of the needle blanks 31 are bent approximately 90° from the longitudinal axis of the needle blank 31 to form tails 33. If desire, the carrier strip 21 may be a continuous endless carrier which is reused during the needle manufacturing process. The strip would have the pilot holes 25 and tabs 26 and needles would be removed from the endless carrier at a convenient stage of the process, and remounted to one or more additional carrier strips. One skilled in the art will appreciate that the needle blanks 31 may also be mounted to the carrier strip 21 by alternate methods, if desired although not preferred, including welding, clips, adhesives, snap fits, and the like. The bandoleer strip could, if desired, be replaced by a member comprising a lattice of two or more wires. The blank cutter/carrier strip cutter machine 30 consists of several machines and operations as described below including a strip forming tool station 39, wherein the pilot holes 25 and tabs 26 are formed, strip preparation tool station 38 wherein the tabs 26 are opened, wire cut-off and strip crimping tool station 39 wherein wire is fed into tabs 26 and blanks 31 are cut and formed, and tail bending station 39A wherein the proximal tail of the needle blank 31 is bent to facilitate rotation in the carrier strip 21.

Next, the carrier strip 21 having needle blanks 31 mounted therein is moved by a conventional gripper feeder mechanism to first shear station 40. Movement of the carrier strip to the work stations is indexed to precisely align each needle blank 31 within any of the work stations in the following manner. The carrier strip 21 has indexing pilot holes 25 punched into the carrier strip 21 by the blank cutter/strip former 30. The pilot holes mate with pilots mounted at each work station which engage the pilot holes. The pilots consist of a moveable pin which extends into the pilot holes 25. The strip 21 is indexed by a strip feed wherein pilot pins enter, engage and lock the carrier strip 21 into a precisely aligned position within a work station tool. Needle blanks 31 may be mounted at different intervals along the carrier strip 21, for sample, from 0.5" to 1.0" intervals. Because of the spatial layout of the tooling, not every needle blank 31 is within a work station at a given time. Some needles will be indexed into a particular work station while other needles will be queued up waiting to enter work stations.

Figure 2A:
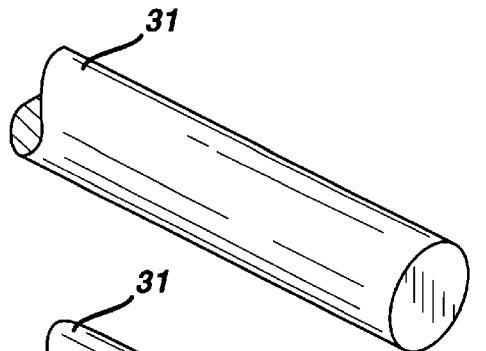
FIGS. 2A–2F illustrate a progression of cross-sectional perspective views of the needle blank after having been processed through each step of the process.
Figure 2B:
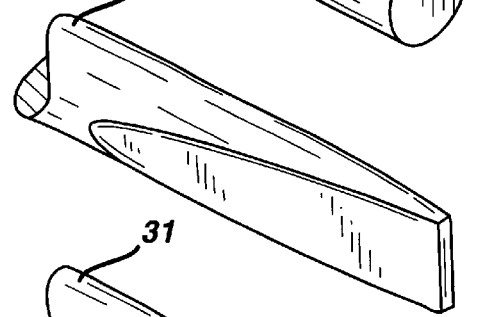
Figure 2C:
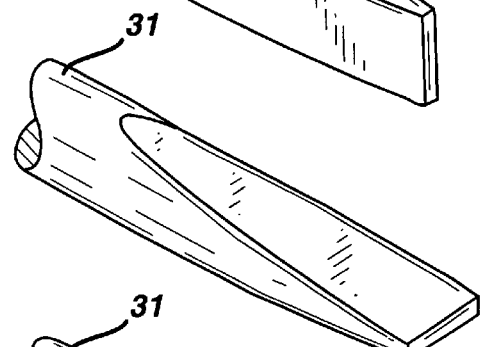
Figure 2D:
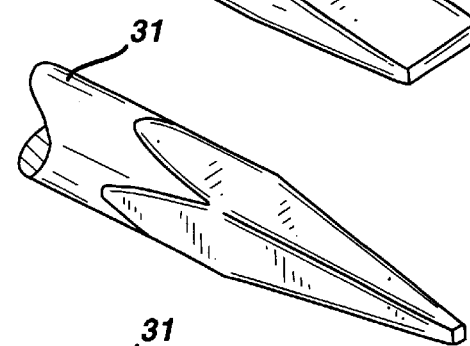
Figure 2E:
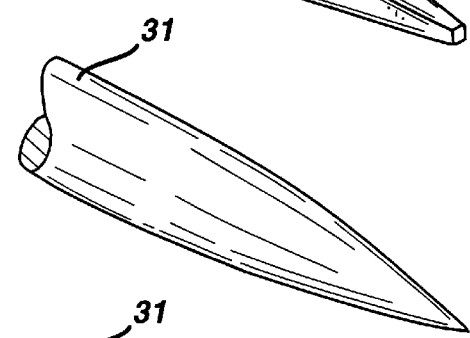
Figure 2F:
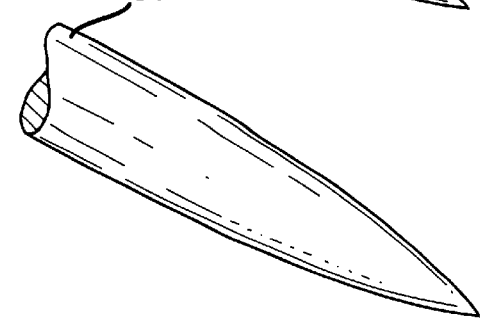
Figure 6:
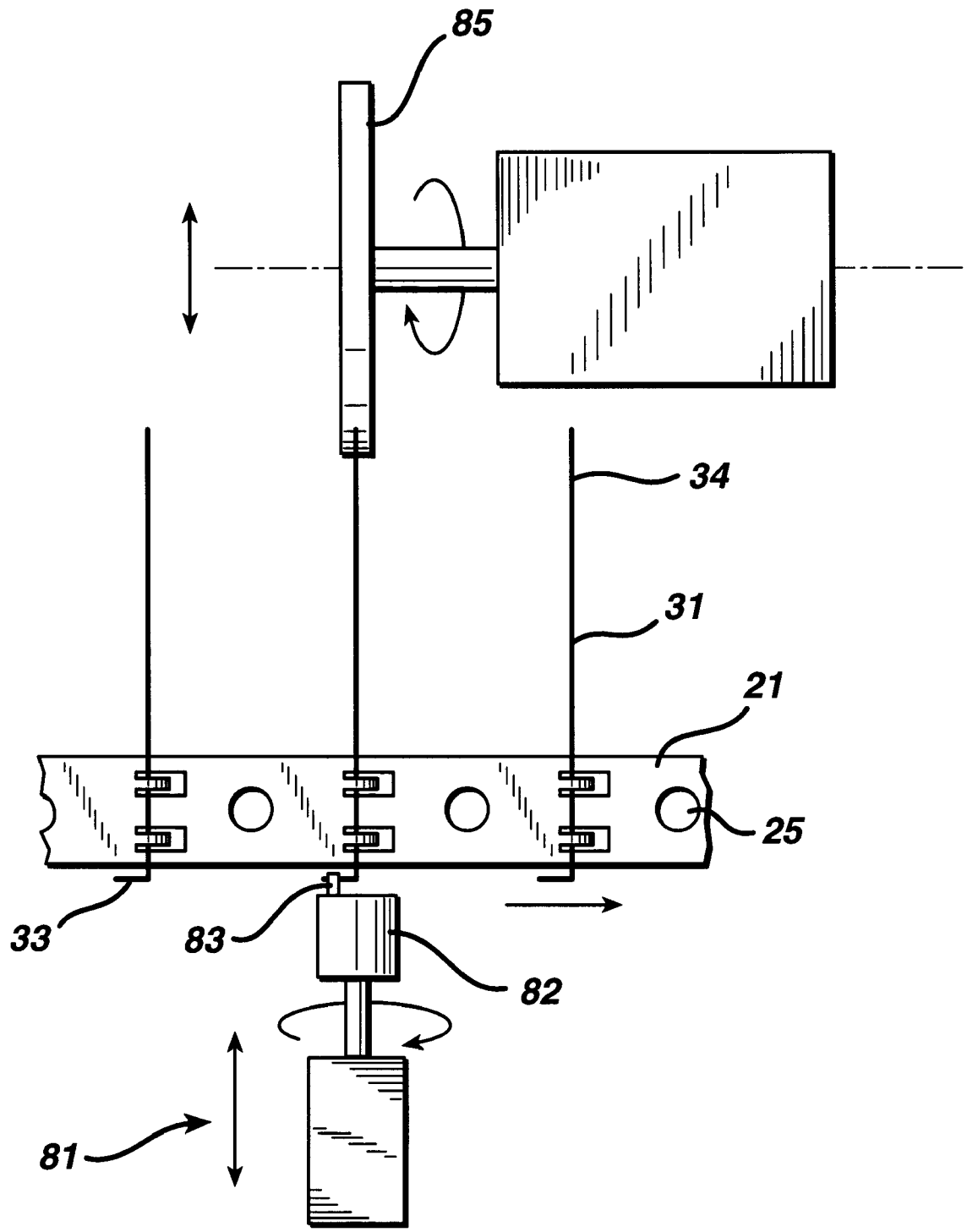
FIG. 6 is a schematic of a tail turn rotary grinding assembly; the needle blank is rotated clockwise in the carrier strip while the rotary wheel grinder grinds the needle in a direction parallel to the longitudinal axis of the needle blank.

Shear station 40 consists of a conventional die and punch. The needle blank 31 is trimmed or sheared in station 40 by having the distal end 34 of the needle blank 31 cut or sheared at an angle, preferably an acute angle, with respect to the longitudinal axis of needle blank 31 along at least one plane and preferably two opposite planes. The needle blank prior to entering shear station 40 will have a distal configuration as seen in FIG. 2A. The needle blank 31 exiting trim station 40 may have a configuration as seen in FIG. 2B. Next, the needle blank 31 is moved to optional station 50 where it is rotated as required to trim the remainder of the needle blank, preferably 90° in the carrier 21 as seen in FIG. 2C. If desired multiple trim stations may be used to form a needle blank 31 having more than four planes trimmed, for example, multiple trims may be used to form a needle blank having a distal cross-section which is n-polyhedral. Next, carrier 21 and the needle blank 31 are moved to shear station 60 where the needle is trimmed along the remaining untrimmed opposed sides to produce a configuration as illustrated in FIG. 2D. If desired, the needle blank 31 can be trimmed only one time to form a single trim plane; or, it may be trimmed more than four times to form multiple planes. The needle blank 31 is then moved to the top and side flattening stations 70 and 75 where the needle blank 31 is appropriately formed by giving it flats. Then the needle blank 31 is moved to a tail turn rotary grind station 80. Referring to FIG. 6, tail turn rotary grind station 80 consists of a tail turning device 81 and preferably a pair of grinding wheels 85, although one grinding wheel may be used. In a preferred embodiment, the device 81 consists of pin 82 mounted to a rotating disc 83 which engages the tail 33 and rotates the needle blank 31 about is longitudinal axis within the carrier strip 21 (see FIGS. 3 and 6). The distal end of needle blank 31 is simultaneously ground to a tapered point by the grinding wheel 85. The needle blank 31 and the wheels 85 are preferably moved with respect to each other during the grinding. Each grinding wheel 85 has one half of the profile of the desired taper point needle configuration. However, if desired, a single grinding wheel may be used or conventional grinding wheels not having a contour may be used. The grinding wheel 85 or wheels 85 may have an angular or other profile. For the sake of clarity, only one grinding wheel 85 is seen in FIG. 6. As the needle blank 31 is turned by the device 81, the grinding wheels 85 grind the distal end of the needle blank 31 parallel to the longitudinal axis of the needle blank 31. The needle blank 31 has a distal configuration as seen in FIG. 2E after exiting grinding station 80. The carrier strip 21 and needle blank 31 are next transported to tail turn rotary grind station 90 for processing similar or identical to that which occurs in tail turn rotary grind station 80 using similar or identical equipment. The needle blank 31 will have a distal configuration as seen in FIG. 2F after having been processed in tail turn rotary grind station 90. The tail turning and wheel grinding speeds will be sufficient to remove material effective to produce the desired taper point configuration. This will depend on material types and sizes as well as grinding medial type and wheel configuration. The grinding medial will typically be coarser in the first grinding station and finer in the second or additional grinding stations. Although not preferred, an alternate method of grinding useful in the process of the present invention is to maintain the needle blank 31 in a fixed configuration in the carrier such as by welding and to orbitally move grinding wheel 85 about the needle blank 31. It will also be appreciated that equivalent material removal devices can be used including shearing device similar in operation to a pencil sharpener and the like.

The term "taper point" as used herein is defined to mean the distal and of a needle or needle blank (or wire member) having a taper profile which tapers from a maximum dimension to a distal minimum wherein the distal point may have a variety of radii ranging from a piercing point to the original diameter of the wire used to manufacture the needle or needle blank (or wire member).

The carrier strip 21 and each needle blank 31 are then moved to the optional multiple curving anvil stations 100, 110 and 120 where the needle blank 31 is given a conventional curved configuration of a surgical needle. Next, the needle blanks 31 are optionally rotated in needle blank rotation station 125 using conventional mechanical means to rotate the blank 31 in tabs 26 of carrier 21 to facilitate, e.g., rolling onto a spool. Then, the needle blanks 31 and the carrier strip 21 are optionally washed in wash station 130. The needle blanks 31 and carrier 21 are then rolled onto a conventional spool in a conventional manner using a conventional spooling apparatus. If desired, the carrier strip 21 containing needle blanks 31 may be cut into strips for further processing. Next, the spool or tray containing needle blanks 31 and the carrier strip 21 is moved to optional spool heat treat station 140 where the needle blanks 31 are heated with or without a controlled gas environment in an oven at a sufficient temperature for a sufficient amount of time to effectively improve the mechanical strength of the needle blanks 31.

Next, the spool or tray containing the carrier strips 21 and the needle blanks 31 are moved to an optional annealing apparatus 150 where the proximal ends of the needle blanks 31 are annealed. The needles are heated in a conventional annealing process at a sufficient temperature and held for a sufficient length of time at that temperature to effectively anneal the proximal ends of the needle blanks 31. One reason annealing may be used is to improve swaging. Annealing apparatus 150 consists of any conventional apparatus including a flame, conventional oven, resistance heating, induction heating, etc.

Next, the carrier strips 21 containing needle blanks 31 are moved to laser drilling station 160. Optionally, the needles are removed from carrier strip 21 and remounted to a second carrier strip. Preferably the needle blanks remain on the carrier strip 21 and the strip 21 with the needle blanks 31 is fed to the laser drilling apparatus. The needle blanks 31 mounted to the second carrier strip are fed to a laser drilling apparatus wherein a suture mounting hole is drilled into the proximal end of each needle blank. The hole which is drilled by the laser is commonly referred to as a blind hole. The suture mounting hole if desired may also be mechanically drilled or drilled through other conventional methods including electron discharge techniques, etc. The loose needle blanks 31 can then be additionally cleaned and the needle blanks may be mounted into an additional carrier. Then, the needle blanks 31 are optionally washed and may, if desired, be placed into an optional electrochemical bath 170. The needle blanks 31 are maintained in the bath 170 for a sufficient time to effectively finish the needle blank 31. The finished needles 180 are then removed from the electrochemical bath 170, and washed if necessary. If desired, the needles 180 may be siliconized at siliconizing station 190 by treating the needles 180 with conventional siliconizing materials in a conventional manner using conventional equipment, e.g., immersion in a tank of siliconizing material.

If desired, the above-described process may be modified by having a single trim step prior to grinding the needle blank. In addition, the process may also be modified by not rotating the needle in the carrier while grinding. In such a case, the grinding would be accomplished with the grinder orbitally rotated about the needle blank. In yet another variation of the above described process, the needle is not ground, the point is formed by shearing or trimming in at least four planes to form a blank having a distal cross-section which is n-polyhedral.

Figure 7:
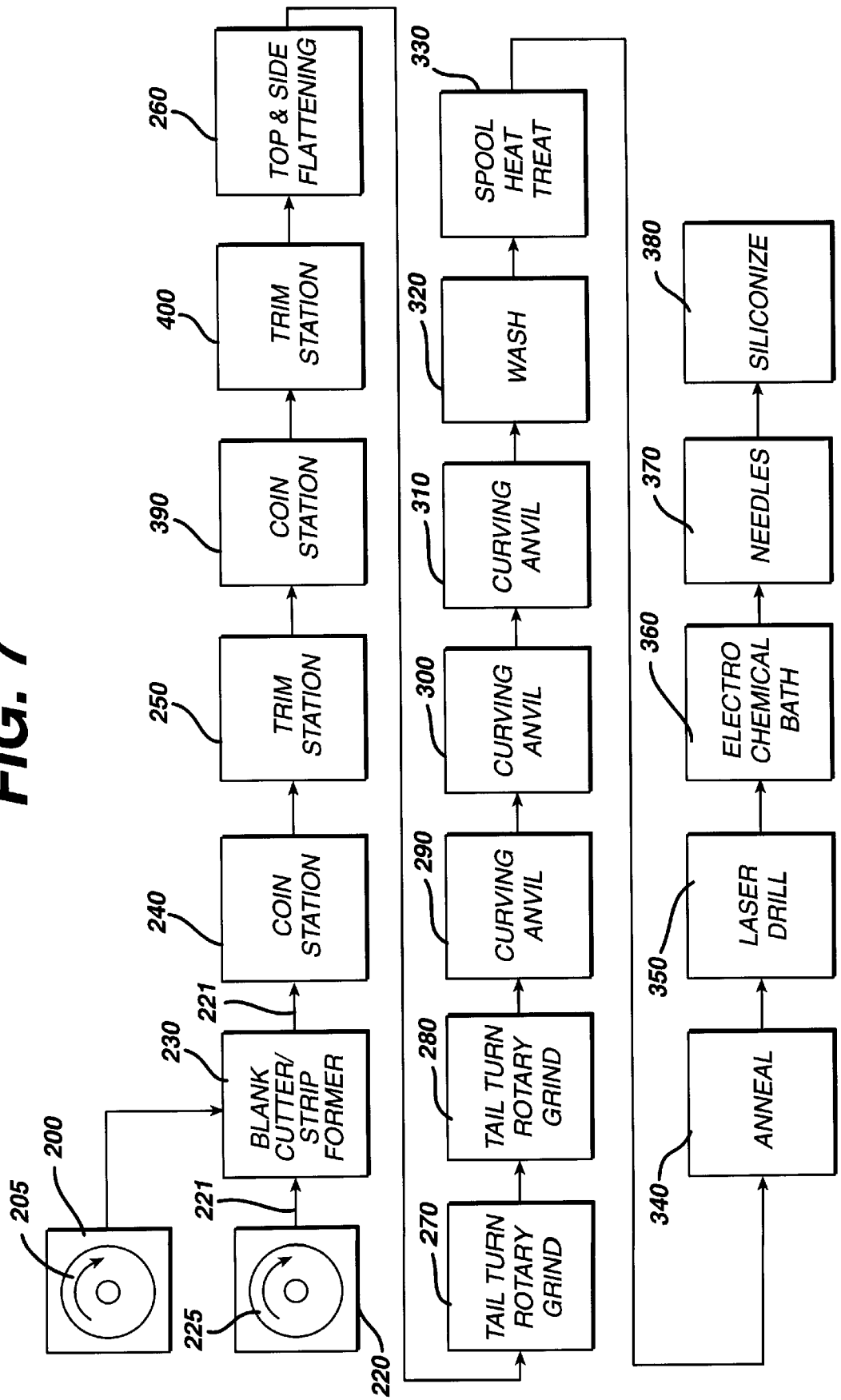
FIG. 7 is a flow diagram illustrating an alternate process for forming taper point needles wherein the needle blanks are coined and trimmed prior to the grinding step.
Figure 9:
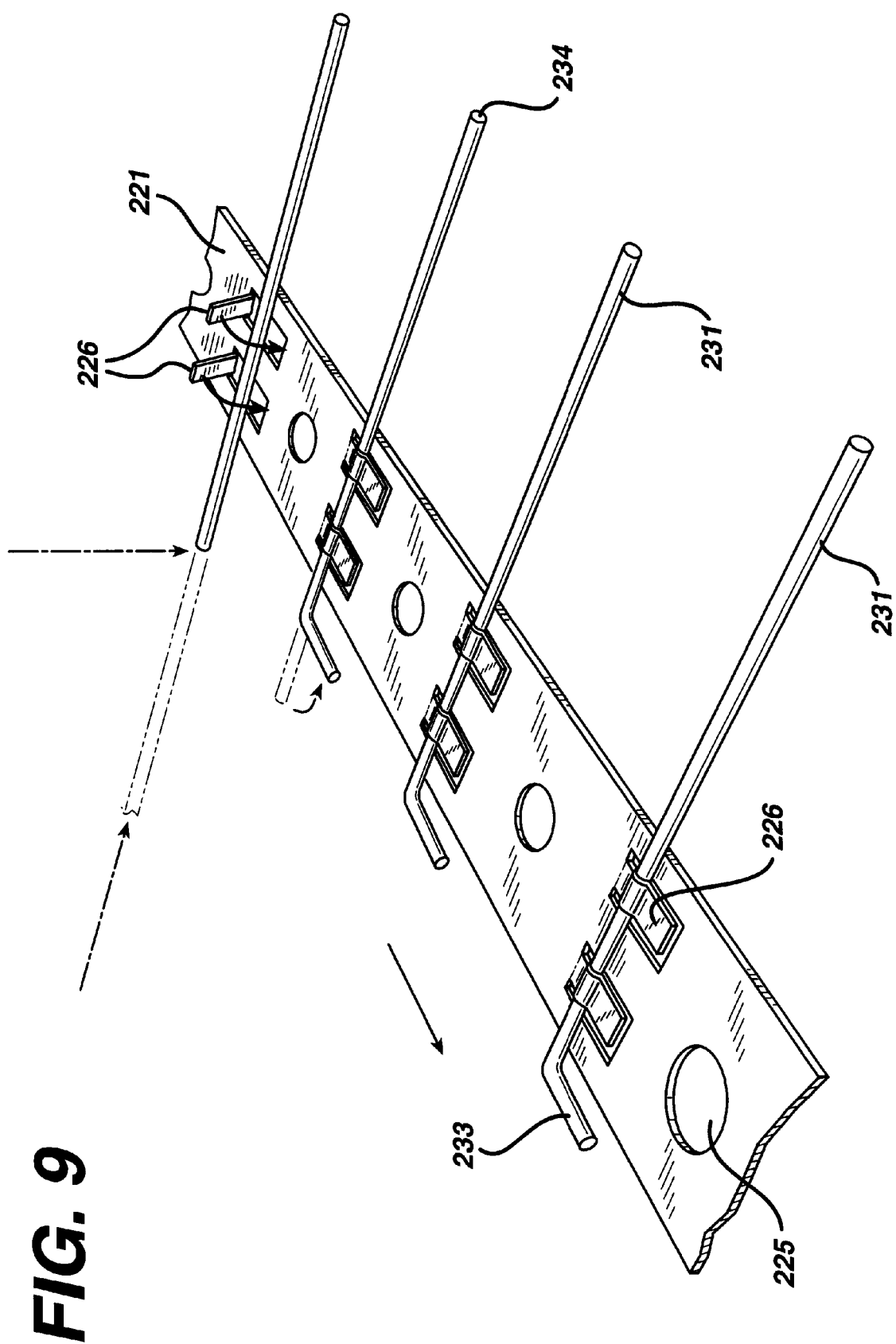
FIG. 9 is a perspective view of a needle blank after it has been cut by the blank cutter/strip former machine; the needle blank is shown mounted in a section of carrier strip with the proximal end or tail bent.
Figure 10:
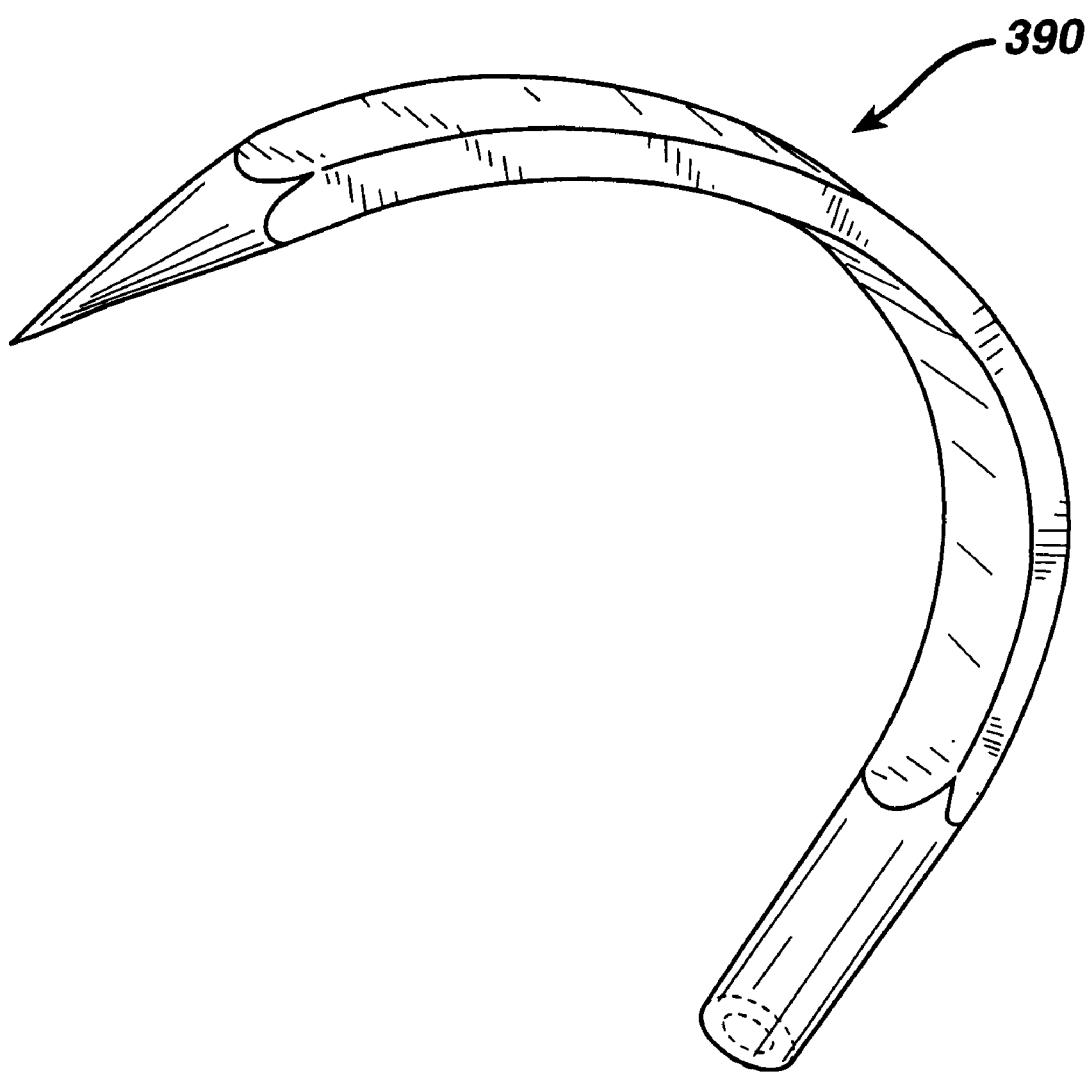
FIG. 10 is a perspective view of a needle produced by the process of FIG. 7.

An alternate process of the present invention is illustrated in FIG. 7. In that process, wire 206 from roll 205 is fed by a conventional gripper/feeder machine 210 to blank cutter/carriage strip former machine 230. The roll 205 is rotatably mounted in gripper/feeder 210. Simultaneously, the carrier strip 221 is fed from carrier strip roll 220, which is rotatably mounted in conventional gripper/feeder machine 225, to blank cutter/carriage strip former machine 230. In blank cutter/carriage strip former machine 230, the wire 206 which is fed from gripper/feeder 210 is cut into lengths which are conventionally referred to as needle blanks 231. As the needle blanks 231 are being cut, the blank cutter/carrier strip former 230 is simultaneously processing the carrier strip 221. The carrier strip 221 typically consists of a steel strip known as a bandoleer. The carrier will be sufficiently thick, sufficiently wide and sufficiently flexible to effectively move and retain needle blanks while being capable of being die punched and formed. Preferably the bandoleer is made of a flexible metal such as cold rolled steel and equivalents thereof. However, the bandoleer may also be made from polymeric materials such as engineered, reinforced polymers and equivalents thereof. The wire 206 being fed from gripper/feeder 210 is cut into lengths which are conventionally referred to as needle blanks 231 within blank cutter/carriage strip former machine 230. As the needle blanks 231 are being cut, the blank cutter/carrier strip former 230 is simultaneously processing the carrier strip 221 in the following manner. Carrier strip 221 is processed to receive needle blanks 231 and to engage indexing controls within the various work stations. The carrier strip 221 is die cut, formed and crimped to produce a carrier strip having indexing pilot holes 225 and crimps which form mounting tabs 206 for receiving, engaging and holding needle blanks 231. Then, the needle blanks 231 are cut and inserted into the mounting tabs 226 of carrier 221 by inserting the wire 206 into each tab 226 and then cutting the wire 206 to form a needle blank 231. The proximal ends 232 of the needle blanks 231 are bent approximately 90° from the longitudinal axis of the needle blank 231 to form tails 233. Referring to FIG. 9, a section of carrier strip 221 containing needle blanks 31 is seen. As mentioned previously in the description of the process of FIG. 1, blank cutter/strip former 230 similarly consists of several work stations.

Figure 8A:
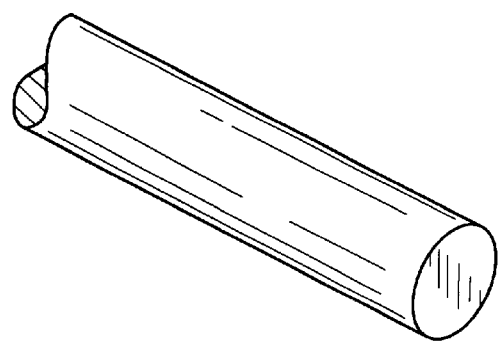
FIGS. 8A–8E illustrate a progression of cross-sectional views of a needle blank after having been processed through each step of the process of FIG. 7.
Figure 8B:
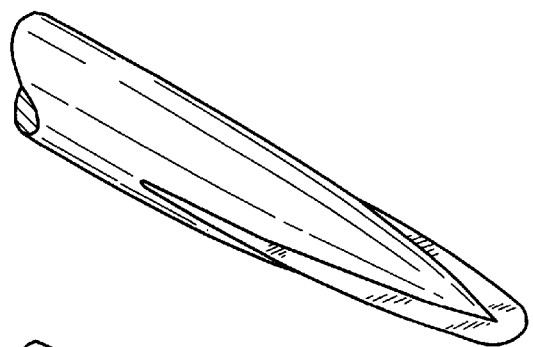
Figure 8C:
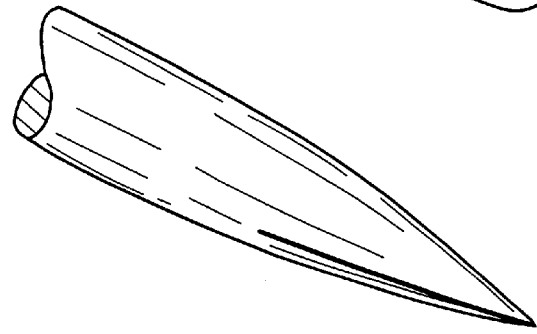
Figure 8D:
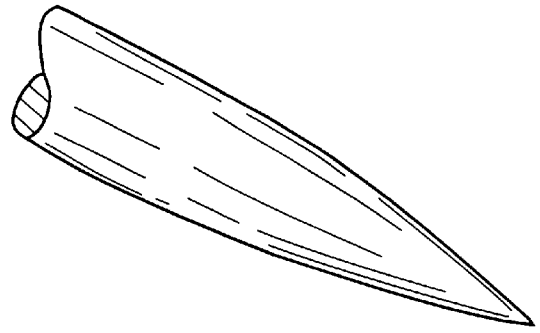
Figure 8E:
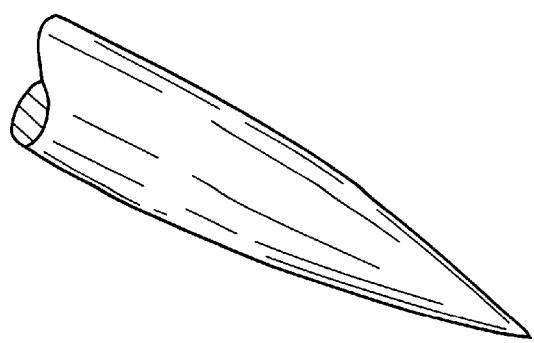
Figure 12:
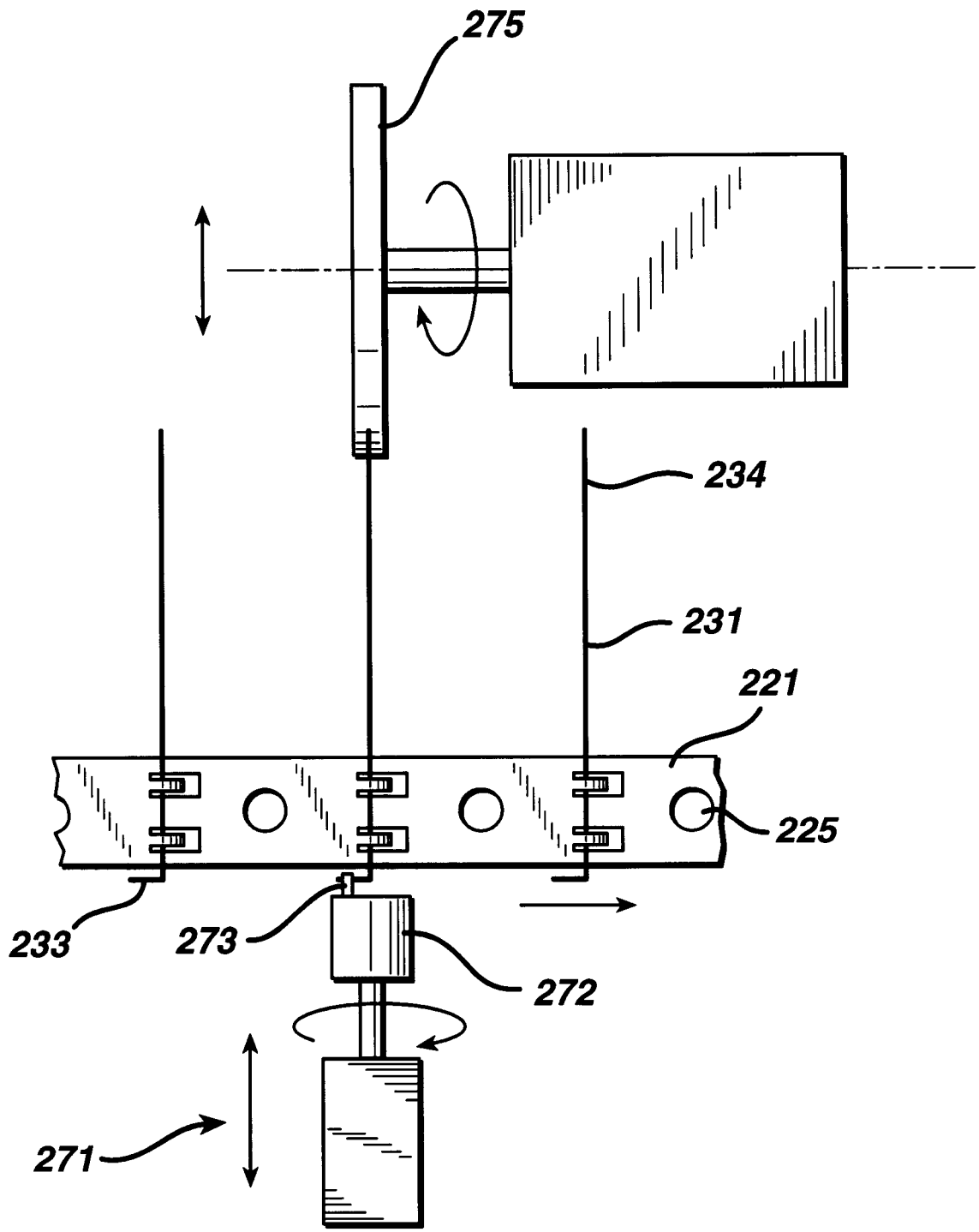
FIG. 12 is a schematic of a tail turn rotary grinding assembly; the needle blank is rotated clockwise in the carrier strip while the rotary wheel grinder grinds the needle in a directional parallel to the longitudinal axis of the needle blank.

Next, the carrier strip 221 having a needle blanks 231 mounted therein is moved by a conventional gripper/feeder mechanism to first coin station 240. Movement of the carrier strip to the work stations is indexed to precisely align each needle blank 231 within any of the work stations in the following manner. The carrier strip 221 has indexing pilot holes 225 punched into the carrier strip 221 by the blank cutter/strip former 230 as seen in FIG. 9. The pilot holes 225 mate with pilots mounted at each work station which engage the pilot holes 225. The pilot consist of a moveable pin which extends into the pilot holes 225. The strip 221 is indexed by a strip feed wherein pilot pins enter, engage and lock the carrier strip 221 into a precisely aligned position within a work station tool. Needle blanks 231 may be mounted at different intervals along the carrier strip 221, for example, from 0.5" to 1.0" intervals. Because of the spatial layout of the tooling, not every needle blank 231 is within a work station at a given time. Some needle blanks 231 will be indexed into a particular work station while other needle blanks 231 will be queued up waiting for enter a work station. Coining station 240 consists of a conventional closed cavity two-piece die set. The needle blank 31 is coined in station 240 by having the distal end 234 of the needle blank 231 hit with the die forcing the material into the cavities of the dies. The needle blank 31 prior to entering coining station 240 will have a configuration as seen in FIG. 8A. The needle blank 231 exiting coining station 240 has a configuration as seen in FIG. 8B. If desired, although not preferred, prior to coining station 240, the needle blank 231 may be optionally coined in an open radius die, i.e., a die without a cavity. Next the needle blank 31 is moved to trim station 250 where it is blanked with a punch and cutting die. The needle blank 31 upon exiting trimming station 250 will have a configuration as seen in FIG. 8C. If so desired, the needle blank 231 may be progressively formed in additional optional coin and trim stations such as coin station 390 and trim station 400 as seen in FIG. 7. The needle blank 231 is then moved to the top and side flattening station 260 where the needle blank 231 is given flat top and bottom sides. Then the needle blank 231 is moved to a tail turn rotary grind station 270. Tail turn rotary grind station 270 consists of a tail turning chuck 271 and a pair of grinding wheels 275. In a preferred embodiment the chuck 271 consists of pin 272 mounted to a rotating disc 273 which engages the tail 233 and rotates the needle blank 231 about its longitudinal axis within the carrier strip 221 (see FIGS. 9 and 12). The distal end 234 of needle blank 231 is simultaneously ground to a tapered point by the grinding wheels 275. Each grinding wheel 275 has one half of the profile of the desired taper point configuration. However, if desired, a single grinding wheel 275 may be used or conventional grinding wheels 275 not having a contour may be used. The grinding wheel 275 or wheels 275 may have an angular or other profile. For the sake of clarity, only one grinding wheel 275 is illustrated in FIG. 12. As the needle blank 231 is turned by the chuck, the grinding wheels grind the distal end 234 of the needle blank 231 parallel to the longitudinal axis of the needle blank 231. The needle blank has a distal configuration as seen in FIG. 8D after exiting grinding station 270. The carrier strip 221 and needle blank 231 are next transported to tail turn rotary grind station 280 for processing similar or identical to that which occurs in tail turn rotary grind station 270 using similar or identical equipment, although the grit sizes of the grinding wheels may be finer. The needle blank 231 will have a distal configuration as seen in FIG. 8E after having been processed in tail turn rotary grind station 280.

The carrier strip 221 and needle blank 231 are then moved to the multiple curving anvil station 290, 300, and 310 where the needle blank 231 is given a conventional curved configuration of a surgical needle. Next, the needle blanks 31 may be optionally turned in the tabs 26 sufficiently to effectively allow rolling the carrier 21 and needle blanks 31 onto a spool. Then, the needle blanks 23 and the carrier strip 221 are optionally washed in wash station 320. The needle blanks 231 and carrier 221 are then rolled onto a conventional spool in a conventional manner using a conventional spooling apparatus. If desired, the carrier strip may alternately be cut into strips for further processing. Next, the spool containing needle blanks 231 and the carrier strip 221 is moved to optional spool heat treat station 330 where the needle blanks 231 are heated with or without a controlled gas environment in an oven at a sufficient temperature for a sufficient amount of time to effectively make the needle blanks 231 more ductile and to improve their mechanical strength.

It is also known in such processes to use a conventional electric arc die forming apparatus to shape the coining dies to conform to the profile of a taper point needle. This shape cannot be mechanically ground in, and it's location in the tools must be precisely located to allow for adequate coining and trimming.

Figure 24A:
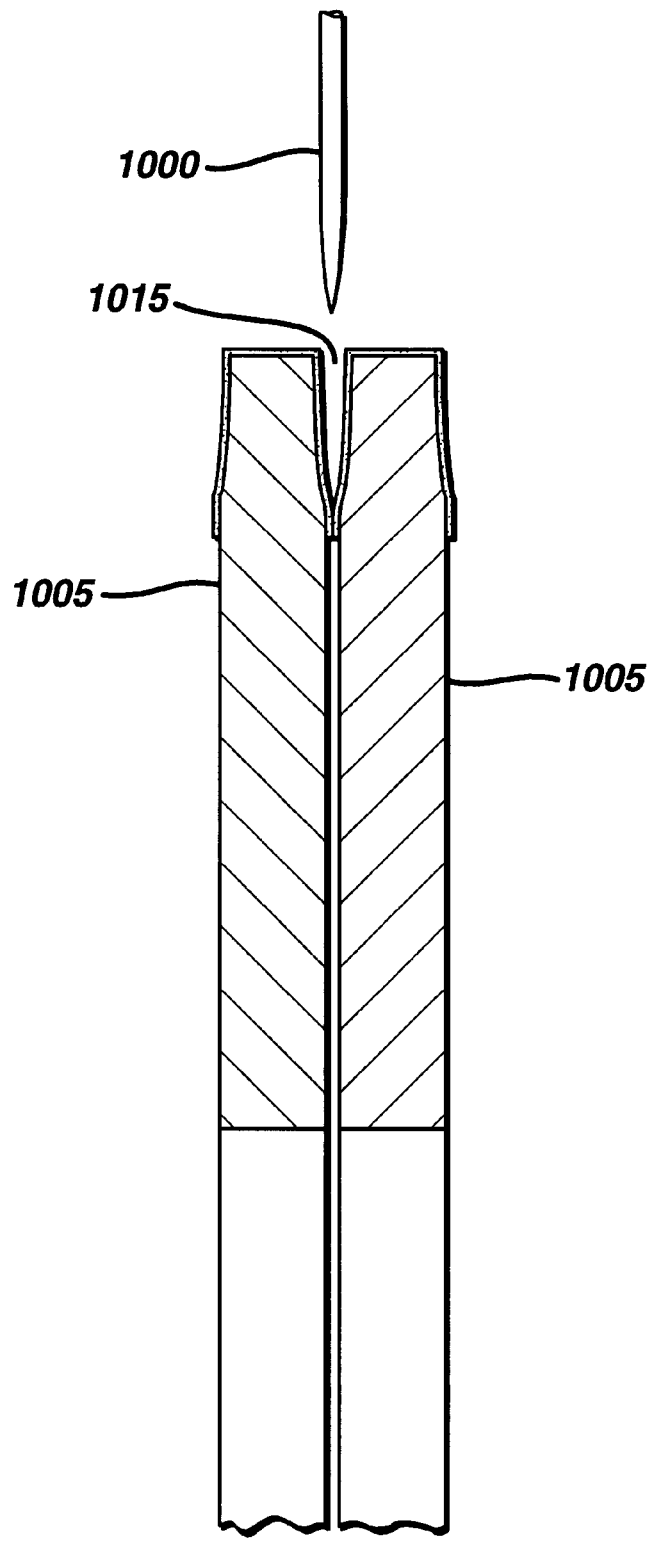
FIG. 24A is a partial cross section of a grinding wheel useful in the process of the present invention illustrating an EDM electrode used to form the grinding groove.
Figure 24B:
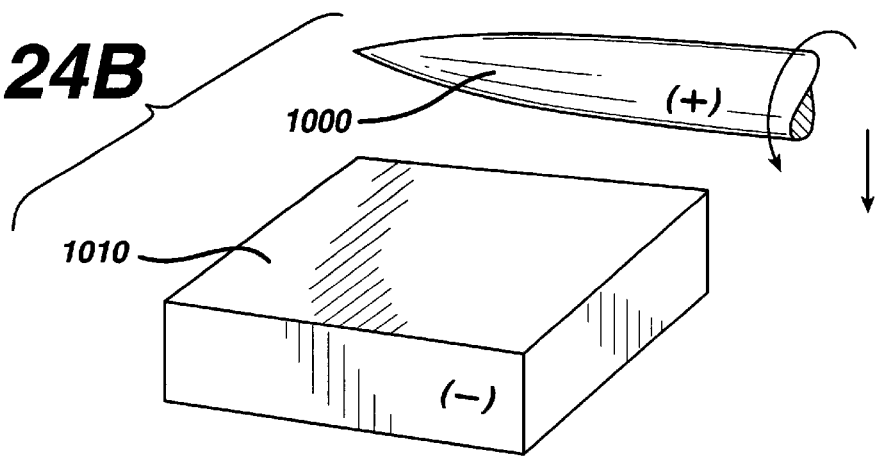
FIG. 24B–E illustrate the formation of a die useful in the practice of the present invention using an EDM having a needle shape.
Figure 24C:
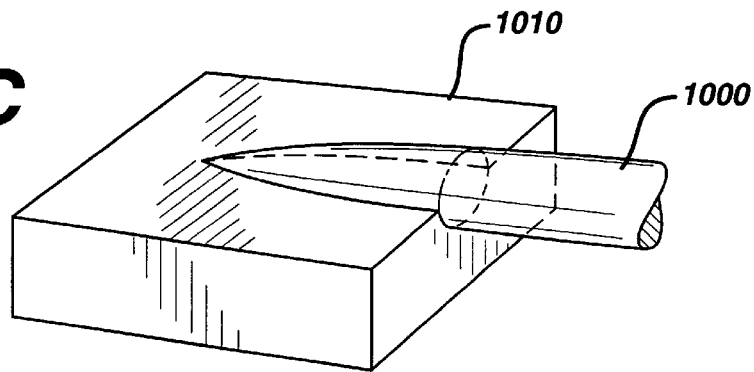
Figure 24D:
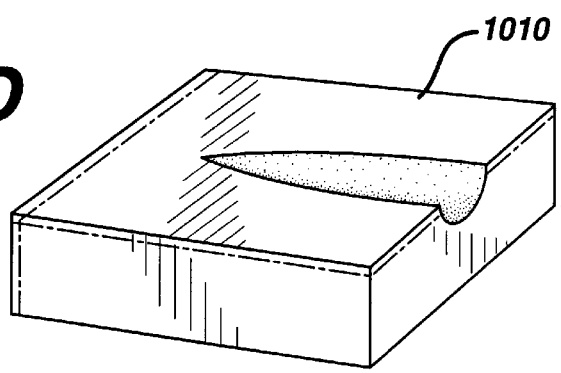
Figure 24E:
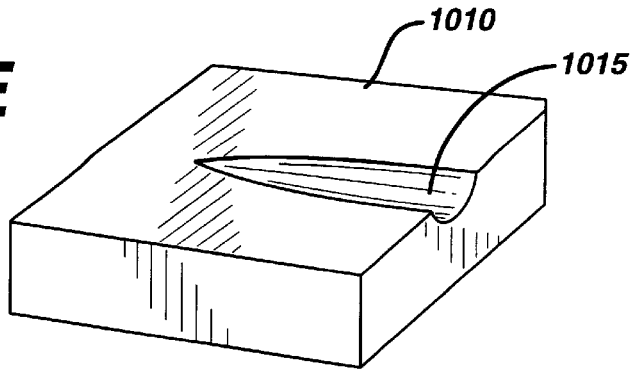

The success of coining taper points on needle blanks relies on the development of a repeatable process to accurately fabricate conical taper point forming dies. Conventional methods require complete custom lapping in the manufacture of these tools. An alternate method was developed utilizing Electric Discharge Machine "EDM" technology (see FIG. 24A–E). The method require the formation of carbon electrodes having the desired contour of the taper point needle to be manufactured. Typical tool grinding is not a practical method to achieve the contours. Alternately, carbon electrodes 1000 are formed using contoured grinding wheels 1005. Once formed, the electrode 1000 is placed in a special rotating head. The head is located over the die blank and slowly lowered. The electrodes slowly erode or burn in the surface of the die blank to form the desired contour in the die blank 1010 (as seen in FIG. 24B). Since the electrodes also erode away as the shape is burned in, new electrodes replace eroded electrodes until the final die cavity 1015 is achieved. The cavity is then polished to improve die life. The outside dimensions of the tool is then sized to fit into a specified cavity or holder within a die set module of high speed stamping equipment.

Next, the spool containing the carrier strips 221 and the needle blanks 231 are moved to an annealing apparatus 340 where the proximal suture mounting ends of the needles are optionally annealed. The needles are heated in a conventional annealing process at a sufficient temperature and held for a sufficient length of time at that temperature to effectively anneal the needle blanks 231. Annealing apparatus 340 consists of a conventional annealing apparatuses as previously described including flame.

Next, the carrier strips 221 containing needle blanks 231 are moved to laser drilling station 350 where a suture mounting hole is drilled into the proximal end of each needle blank 231. The hole which is drilled by the laser is commonly referred to as a blind hole. Then, the needle blanks 231 are optionally placed into an electrochemical bath 360 and are maintained in the bath 360 for a sufficient time to effectively finish the needle blanks 231. The finished needles 370 are then removed from the electrochemical bath 360. If desired, the needles 370 may be siliconized at siliconizing station 380 by treating the needles 370 with conventional siliconizing materials in a conventional manner using conventional equipment, e.g., immersion in a tank of siliconizing material.

If desired, the process of FIG. 7 may be modified by eliminating the trim station after the initial coining station. In addition, the process may also be modified by not rotating the needle in the carrier while grinding. In such a case, the grinding would be accomplished with the grinder orbitally rotated about the needle blank. In yet another variation of the above described process, the needle is not ground and the point is formed by shearing or trimming in at least four planes to form a blank having a distal cross-section which is n-polyhedral.

The above-described processes may also be used to manufacture wire members having ends with taper points. Typically the processes would be identical wherein wire blanks would be cut from a spool of wire and progressively formed as described above. The heat treatment and curving steps could be omitted depending upon the application. In addition, one or more grinding steps could be omitted depending upon the nature and types of wire stock utilized to make the wire blanks. Such processes could be used to manufacture, for example, semiconductor leads, fasteners, pins, etc.

The terms "coined" and "coining" as used herein are defined to mean forming or reshaping a metal member by applying sufficient pressure to the member to effectively cause the metal to flow into a cavity or onto a surface of a die and to thereby assume, in whole or in part, the shape of the cavity or the surface of the die.

The needle wires which can be used in the process of the present invention include conventional needle wires made from metals such as 300 series stainless steel, 400 series stainless steel, or any other wire which can be formed including conventional or known alloys.

The diameter of the needle wire used in the process of the present invention will have a diameter which will depend upon the particular alloy used. For example, the needle wire may have a diameter ranging from 0.001 inches to about 0.100 inches. More typically, wires having a diameter of about 0.010 inches to about 0.080 inches may be used, preferably about 0.015 inches to about 0.080 inches. However, other diameters be used. The length of the needle blank 31 will vary in accordance with the type of needle which is being manufactured. The length of the needle blanks will vary in accordance with several parameters including the wire diameter, desired finished length and the type of needle.

The curving anvil machines used in the process of the present invention are conventional curving machines which operate in a conventional manner. The curving anvil machines may consist of forming elements having the desired radii. The curving anvil machines are mounted to a support frame.

The cleaning bath operates in the following manner. The carrier strip and needle blanks are placed into a reservoir containing a conventional aqueous cleaning solution such as an aqueous solution of a conventional non-caustic detergent. A conventional ultrasonic transducer is mounted in the reservoir. A conventional ultrasonic generator drives the transducer. The needle blanks and strips are rinsed and dried prior to removal from bath using a clear hot water rinse followed by a high velocity air flow.

A carrier strip cutter, if used in place of spooling, operates in the following manner. As the carrier strip is fed into the carrier strip cutter, a conventional die and punch is used to cut the strip into pre-determined lengths.

The heat treatment apparatus operates in the following manner utilizing the following cycle. Rolls of carrier containing needle blanks are placed onto trays. The trays are then loaded into a conventional heat treatment oven. The oven is brought to a sufficiently high temperature for a sufficient length of time to effectively heat treat the needle blanks. The process cycle temperatures and times are conventional in the art for processing metals.

The annealing apparatus used in the present invention consists of a conventional apparatus as previously described. The laser drilling apparatus consists of any conventional laser system having sufficient power and accuracy to effectively and repeatedly drill blind holes in needle blanks or needles.

The electrochemical bath apparatus consists of a conventional anodic electrochemical bath. Residence time of the needle blanks in the bath will be sufficient to effectively remove any residual material which may be present on the needle blank 31 to improve the surface finish. The chemical composition of the bath and voltages are conventional in this art. The electrochemical bath mixture comprises an aqueous, acidic mixture.

The electrochemical bath operates in the following manner. The needles are placed upon a metal conveyor belt which transports the needles through the aqueous bath or a sufficient amount of time at a sufficient voltage to effectively remove residual material such as residual metal flash from the needle blanks, thereby forming the finished needles.

Figure 5:
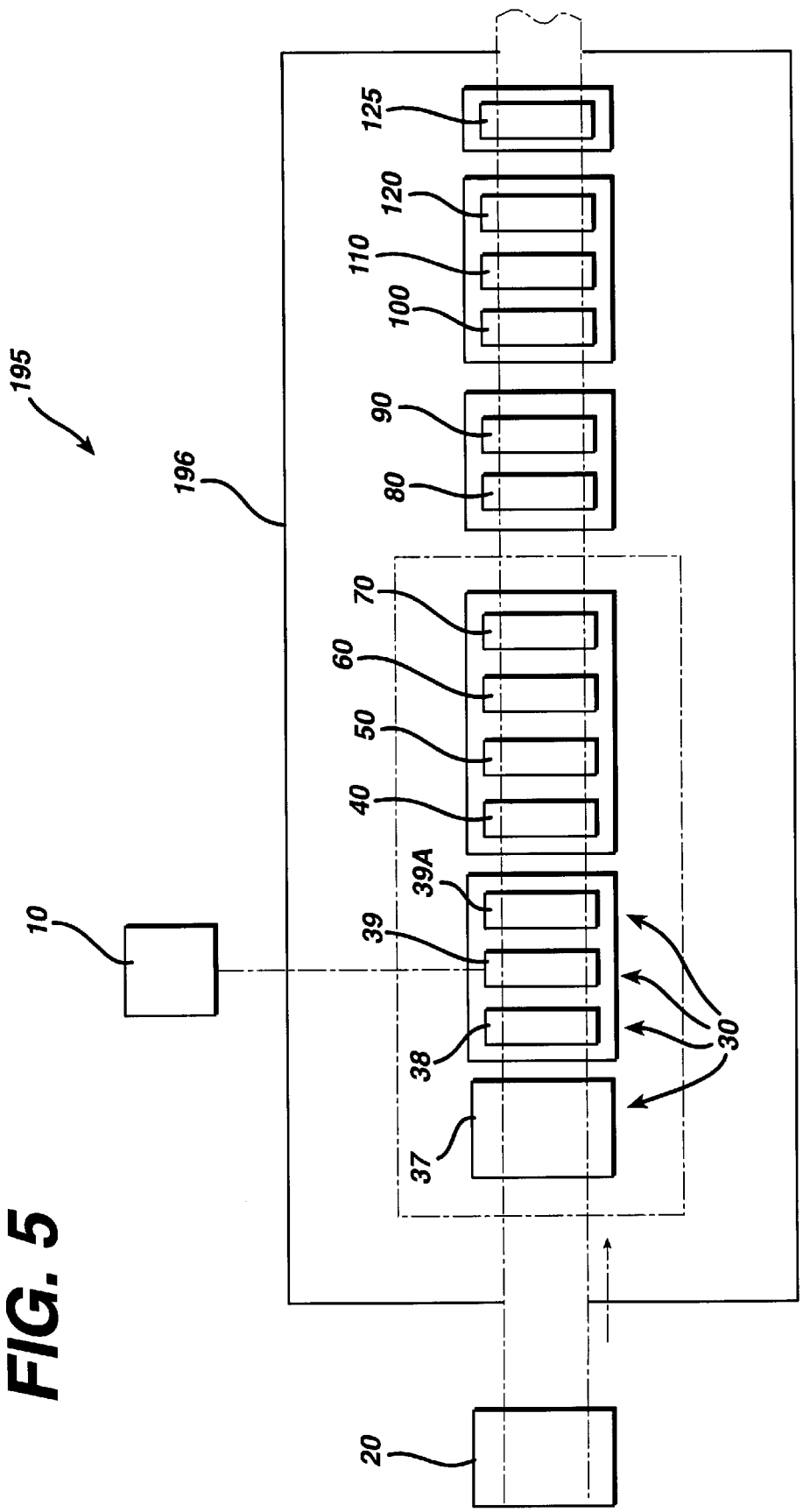
FIG. 5 is a schematic of a layout of the equipment used to manufacture a needle using the process of FIG. 1.
Figure 11:
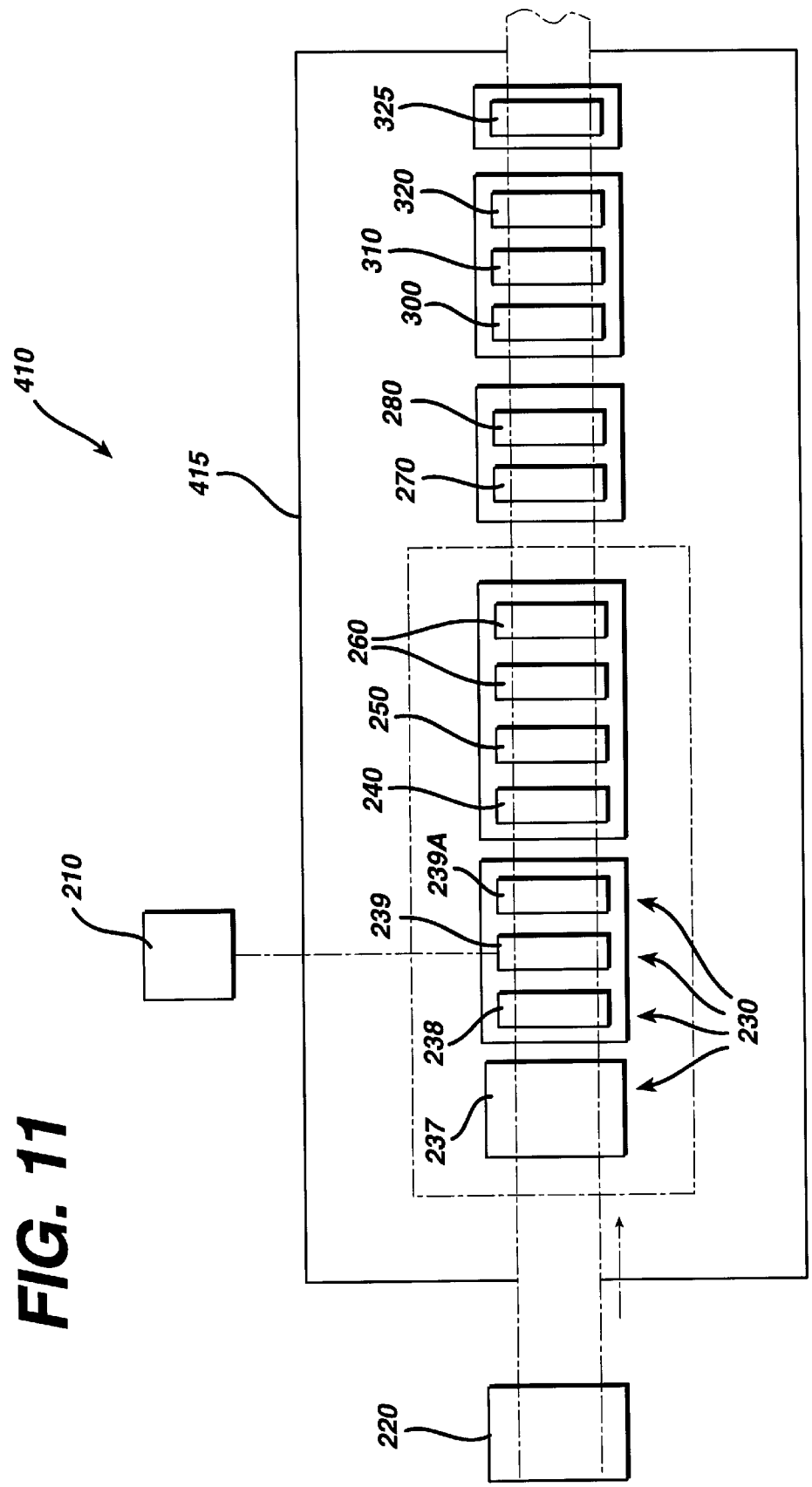
FIG. 11 is a schematic of a layout of process equipment used to manufacture a needle using the process of FIG. 7.

The coining stations, grinding stations and trimming stations utilized in the process of the present invention will consist of punches and dies mounted to frames which are in turn preferably mounted to a unitary forming machine (see FIGS. 5 and 11). It will be appreciated that in automated progressive forming processes of the type described, a needle blank will be successively moved through the various work stations. At any given time as a needle blank 31 enters a particular station there will be other needle blanks entering a subsequent or previous stations. All of the stations are operating on different needle blanks at substantially the same point in time so that, for example, as the needle blank 31 is moved to the shear station 40 from the blank cutter/carriage strip former 30, a needle blank 31 is being moved to the curing anvil 110 from tail turn rotary grind station 90. The cleaning baths, the spool heat treatment stations, the annealing apparatuses, the laser drilling apparatuses, and the electrochemical bath 170 are typically not mounted to the forming machine.

The forming machine 195 used in the process of FIG. 1 consists of a central frame or base 196. Mounted to the base 196 are the various work stations which consist primarily of punches and dies and the grinders 85. The punches and dies are powered in a conventional manner. For example, the work stations may be powered by a motor which powers a flywheel having a clutch which in turn transmits power to the work stations with shafts, spur gears and bullgears. Flywheel is also used to create motion to drive various elements in multiple directions to facilitate the process, e.g., wheels are moved in and out along with guides, and other motions are utilized. The grinders 85 are powered by electric motors. The blank cutter/strip former station 30 is seen to consist of four individual stations including strip forming tool station 37, strip preparation tool station 38 and wire cut-off and strip crimping tool station 39 and tail bending unit 39A. A schematic of the layout of the forming machine 195 is seen in FIG. 6. Sufficient force is exerted upon the dies by the punches to effectively coin the wire blanks at each coining station. The forces will depend on the wire material, wire diameters, tool configuration, die configuration, etc. Typically the forces will range from up to about 30 tons or more. However, it will be appreciated that the forces may vary higher or lower depending upon the configuration of the dies and the diameter and material of the needle blank 31. The forming machine 195 will preferably have a modular configuration wherein various stations can be added, removed or interchanged as desired to vary the process.

A similar layout for the forming machine 410 used to manufacture needles in the process of FIG. 7 is seen in FIG. 11. The forming machine 410 will operate in a manner similar to that of machine 195. The forming machine 410 has frame 415. The machines are identical except that machine 410 will have coining and trimming stations instead of shear stations. Mounted to the base 415 are the various work stations which consist primarily of punches and dies and the grinders 285. The punches and dies are powered in a conventional manner. For example, the work stations may be powered by a motor which powers a flywheel having a clutch which in turn transmits power to the work stations with shafts and bullgears. The grinders 285 are powered by electric motors. The blank cutter/strip former station 230 is seen to consist of four individual stations including strip forming tool station 237, strip preparation tool station 238 and wire cut-off and strip crimping tool station 239 and tail bending machine 239A. A schematic of the layout of the forming machine 410 is seen in FIG. 11. The forming machine 410 will preferably have a modular configuration wherein various stations can be added, removed or interchanged as desired to vary the process.

Figure 13:
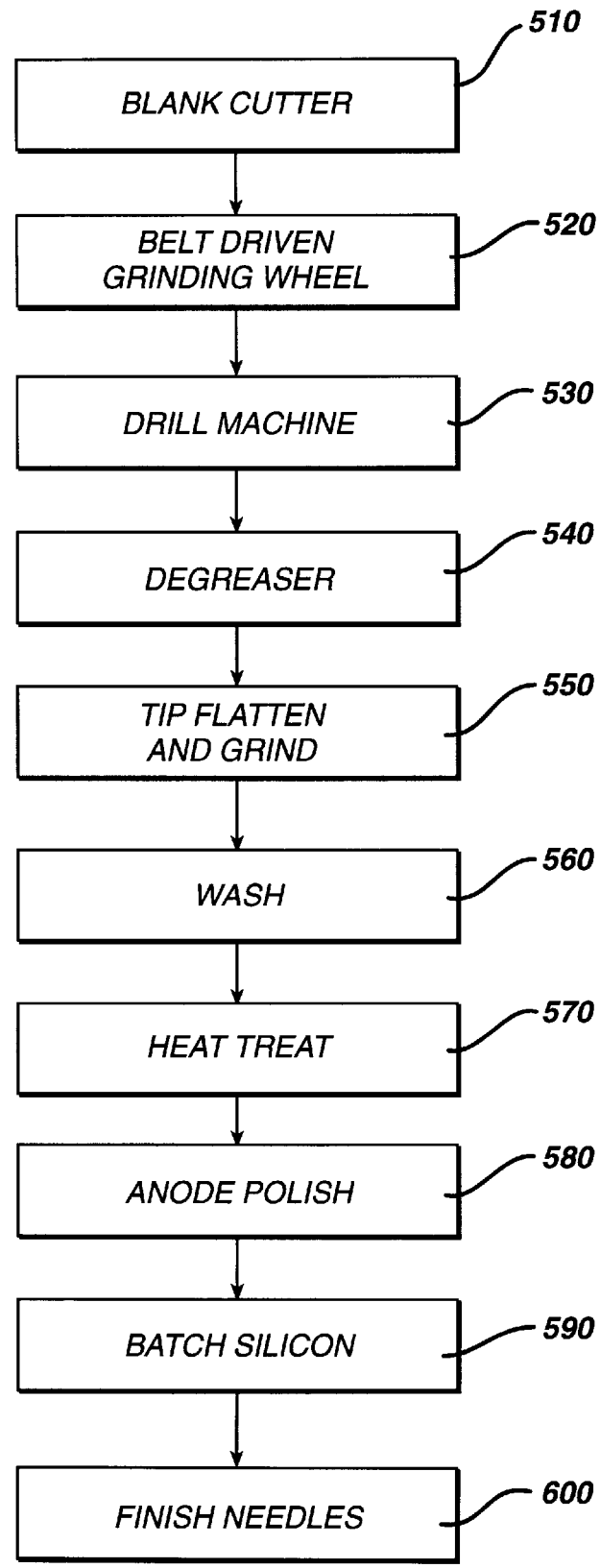
FIG. 13 is a flow diagram illustrating a prior art process for manufacturing taper point needles.
Figure 14A:
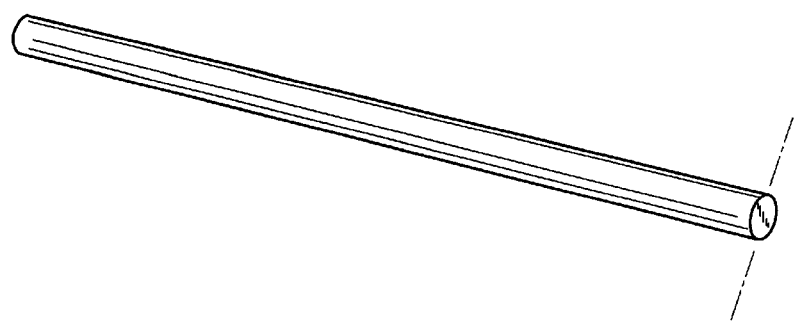
FIGS. 14A–14D depict a progression of cross-sectional views of a needle blank after having been processed through each step of the prior art process of FIG. 12.
Figure 14B:
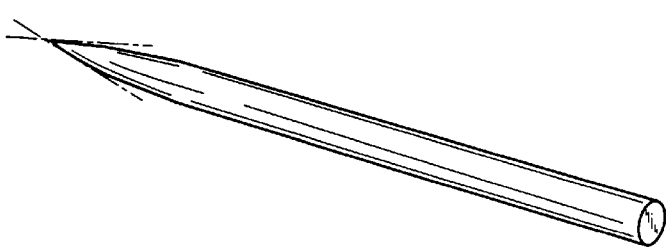
Figure 14C:
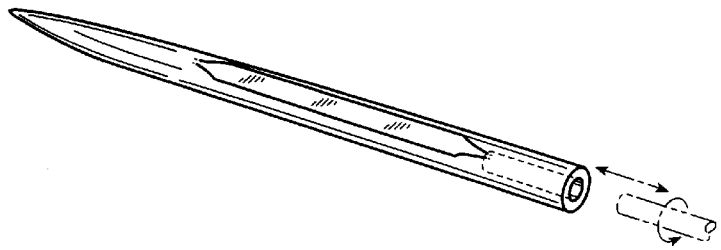
Figure 14D:
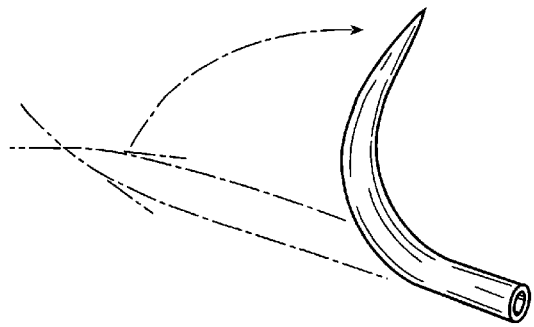
Figure 15:
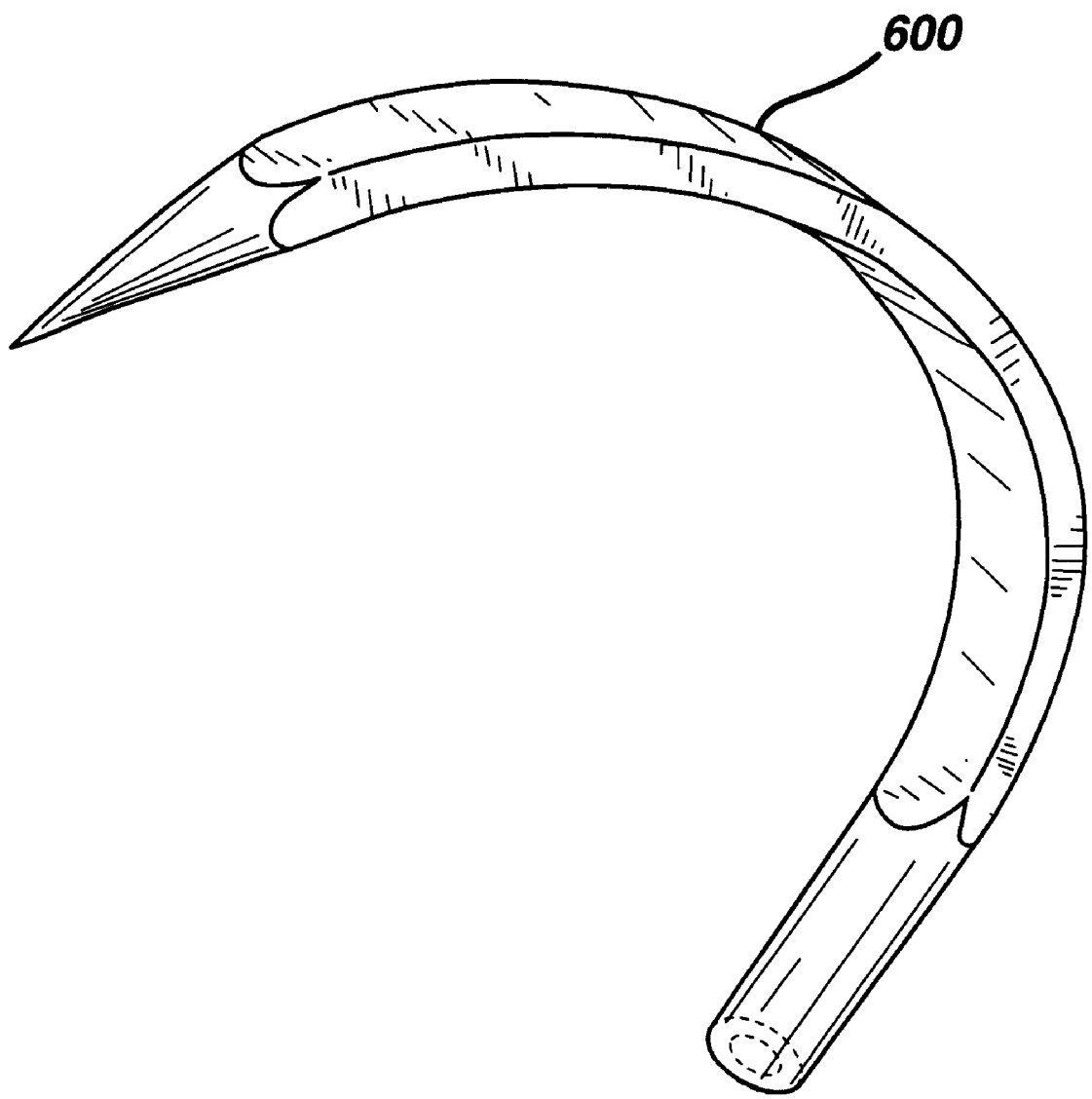
FIG. 15 is a perspective view of a needle manufactured by the prior art process of FIG. 12.

A process of the prior art for manufacturing taper point needles illustrated in FIG. 13. In that process needle blanks 500 are cut from a spool of wire in blank cutting machine station 510 and placed into a bulk container. A needle blank 500 prior to processing is illustrated in FIG. 14A. Initially, the blank 500 is given a rough distal taper point in first belt driven grinding wheel machine 520 as illustrated in FIG. 14B. The needle blanks 500 are then transferred in bulk and mounted into individual chucks in drilling machine 530. The needle blank 500 has a configuration as seen in FIG. 14C after the drilling operation in machine 530. Next the needles are degreased at station 540 in a conventional degreasing apparatus. Then the needle blanks 500 are moved in bulk to machine station 550 wherein the final curved configuration given to each needle blank 500 and the final tip is ground onto the needle blank (see FIG. 14D). The needle blanks are also given flat tops and bottom sides at station 550. Then the needles are moved in bulk to conventional heat treatment station 570, anode polish station 580 and batch siliconization station 590 to produce finished needles 600. A finished needle 600 is seen in FIG. 15.

There are numerous disadvantages associated with the process of the prior art. The disadvantages include low manufacturing and process throughput speeds, inconsistency and manufacturing tolerance variation. In addition, the prior art process may subject needles to process damage, including point dulling. Another disadvantage is that the process equipment utilized in the prior art process tends to have inherent process variability due to the equipment design. Furthermore, the prior art process requires frequent material transfer in the form of loose needle blanks from machine to machine.

Figure 16:
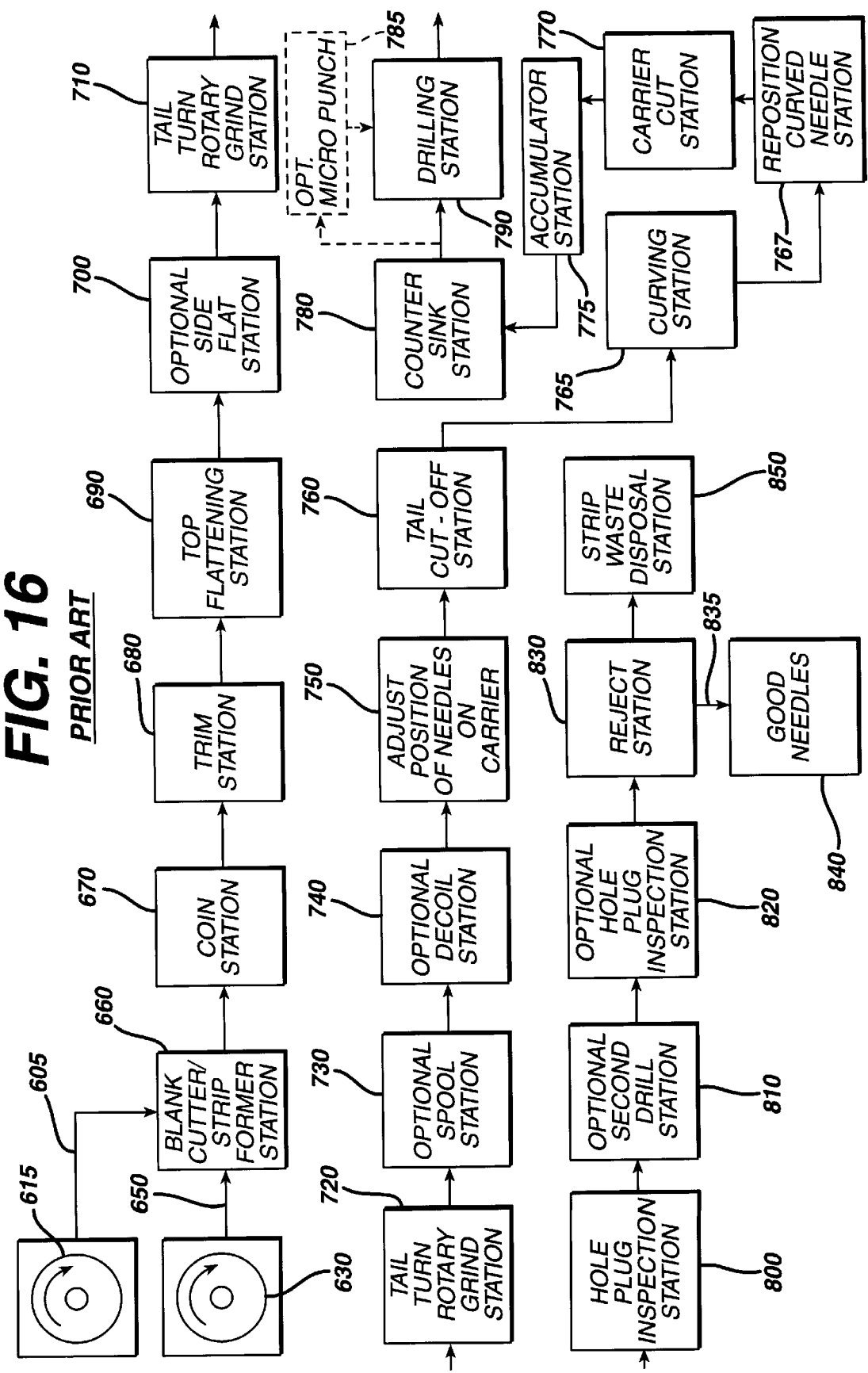
FIG. 16 is a schematic diagram of a prior art drilled needle manufacturing process.

Another prior art process for progressive forming of surgical needles is seen in FIG. 16. As in the prior art progressive forming processes, a spool of wire 605 is loaded into spool unwinding station 615 while a spool of metal strip 650 is mounted in strip unwinder 630. The strip 650 and the wire 605 are moved to blank cutter/strip former station 660 wherein the wire 605 is cut into blanks 610 and strip 650 is die cut into carrier strip 655. Needle blanks 610 are held on carrier 655 by tabs 657. Then, the carrier strip 655 and needle blanks 610 are moved to coin station 670 wherein the distal end of each blank 610 is coined in a die to produce a distal pointed end having lateral flash wings extending outwardly. The coin is such that the needle blank is relieved distally to form a distal nub 905 and the lateral wings are not of constant thickness. Next the needle blanks are moved to trim station 680 where the lateral wings are die cut from each needle blank 610. Next the needle blanks 610 are moved to conventional top flattening station 690 to flatten the tops of the needle blanks 610 and then to optional side flattening station 700. Then, the needle blanks 610 are moved to successive tail turn rotary grind stations 710 and 720 where the needle blanks 610 are given tapered piercing points. At this stage in the process, the needle blanks 610 and carrier 655 may be directed to a proximal suture mounting hole drilling operation or may be optionally coiled and stored prior to drilling. If desired, the needles are spooled at spool station 730 and then decoiled at decoil station 740. Next the position of the blanks 610 is adjusted on the carrier 655 by rotating the needles and positioning the needle blanks 610 so that the tails can be cut off in tail cut station 760. Next the carrier 655 and needle blanks 610 are moved to curving station 765 where the needle blanks 610 are curved in a conventional manner to provide a curved surgical needle profile. The carrier 655 and needle blanks 610 are then moved to reposition station 767. The carrier 655 and needle blanks 610 are then moved to carrier cut station 770 where a section 657 of carrier 655 is continuously cut away to form carrier 658 and to allow drilling, also cut off are the proximal ends of the needle blanks 610. The needle blanks and carrier 658 are then moved to an accumulator station 775. The accumulator station allows the carrier strip to advance in a continuous manner and to feed the needles into countersink station 780 in an intermittent fashion. The needle blanks 610 and carrier 658 are then moved to counter sink station 780 where a bank of four conventional helical drills countersinks the proximal ends of four needle blanks 610 simultaneously. Optionally, the carrier and needles are moved to optional micropunch station 785. Then, the countersunk needles are moved four at a time to the drilling station 790 where a bank of four conventional mechanical drills is used to simultaneously drill the proximal ends of the needle blanks 610 to a desired depth suitable for suture mounting, thereby producing needles 620. Next, each drilled needle 620 is sent to hole plug inspection station 800 where a conventional spring loaded mechanical plug is inserted into each hole to determined whether the depth is adequate. Optionally, the holes may be drilled in segments by moving the needle blanks 610 to successive drilling stations 810 and inspection stations 820. If next, good finished needles 620 are removed at station 830 into bin 840 from carrier 658 and the bad rejected needles are left on the strip and strip may then be chopped for scrap or otherwise discarded. Optionally, the carrier and needles 620 are moved to reject station 830 where bad rejected needles 835 are removed, and then the carrier 658 and needles 620 are moved to spool station 850 for coiling. The coiled needles 620 and strip 658 may be further processed in conventional heat treatment, surface polishing and degreasing steps.

Figure 18A:
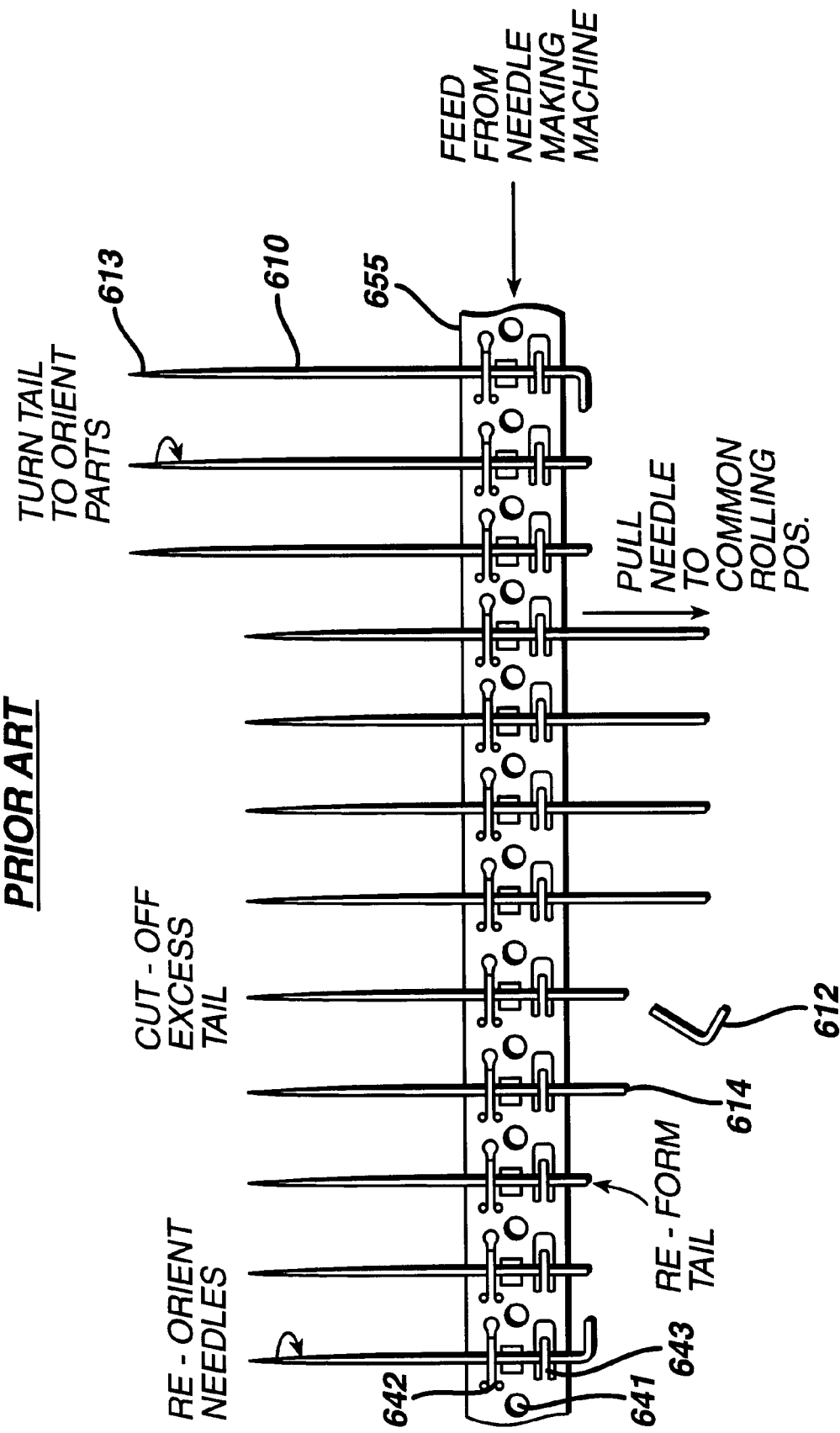
FIGS. 18A and 18B are a schematic of a carrier strip and needles illustrating the steps of the prior art process of FIG. 16.
Figure 18B:
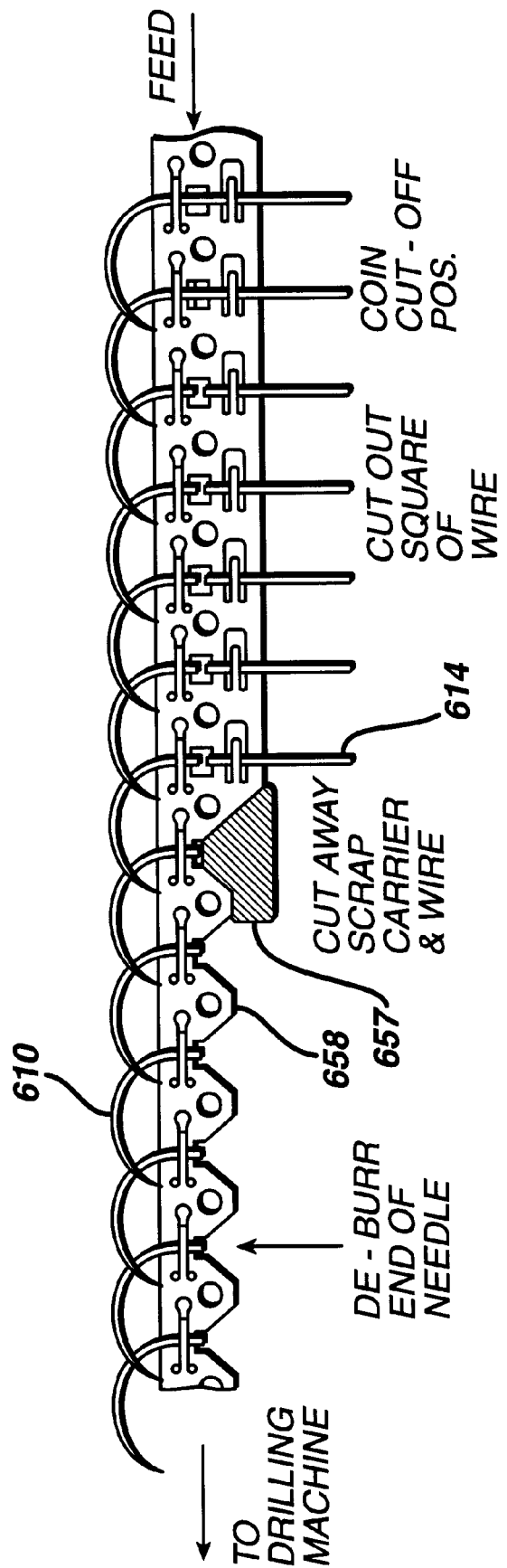
Figure 19A:
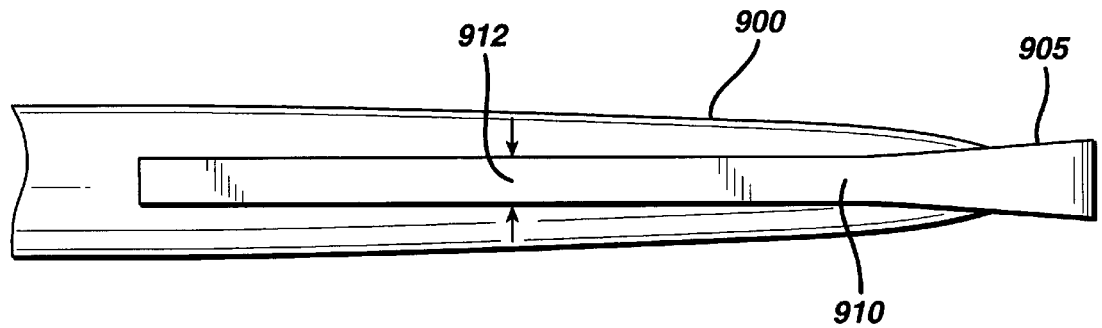
FIGS. 19A–D are magnified partial views of in-process needles illustrating the constant thickness lateral wings of the needle blanks of the present invention illustrating constant thickness lateral wings.
Figure 19B:
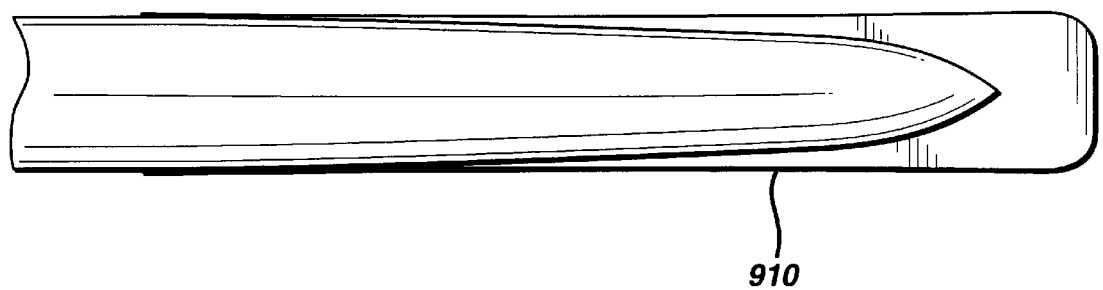
Figure 19C:
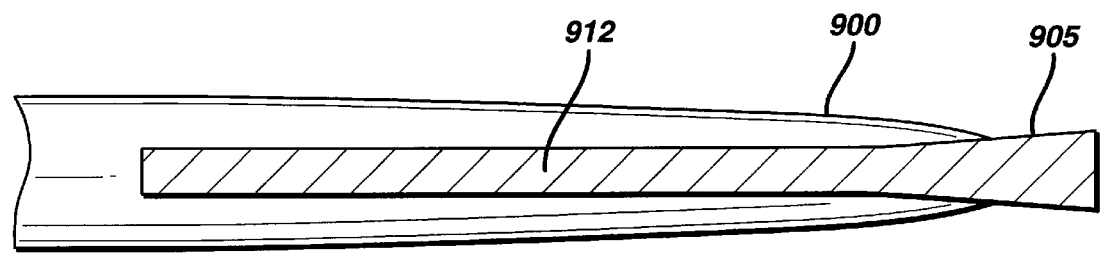
Figure 19D:
Figure 20A:
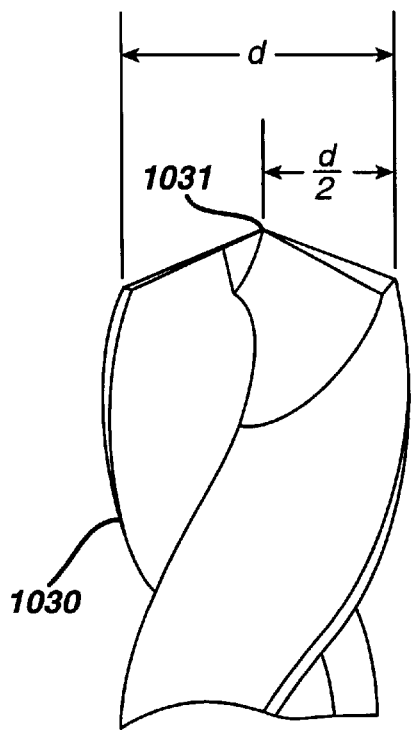
FIG. 20. is a side view illustrating the distal ends of a "centered" drill and an "off-center" drill along with the drilled holes which they produce.
Figure 20C:
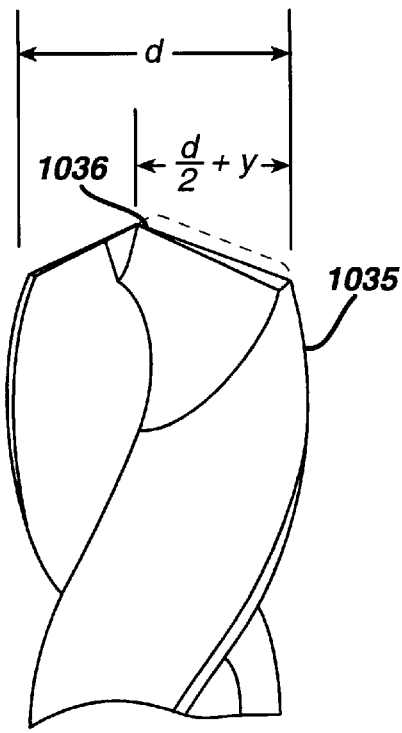
Figure 20B:
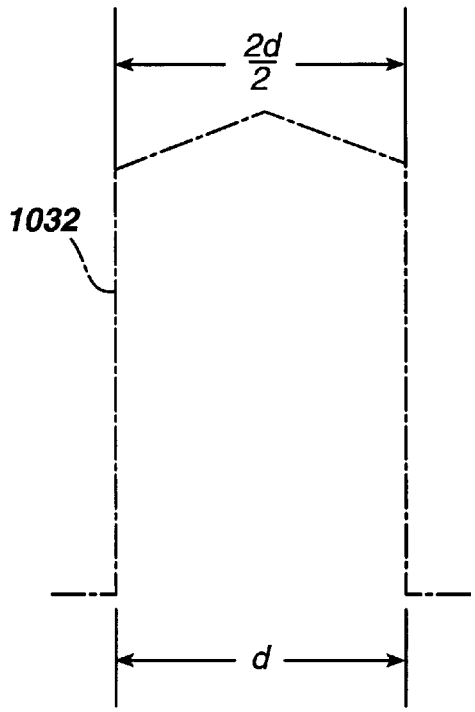
Figure 20D:
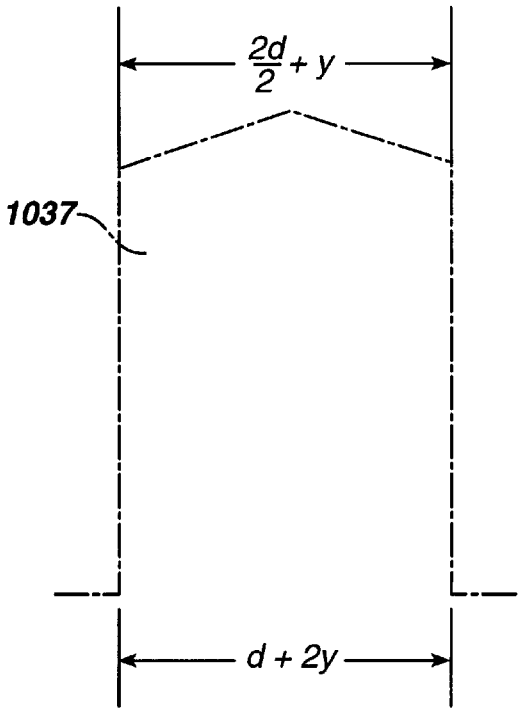

Referring to FIG. 18, the carrier strip 655 and needle blanks 610 are seen in step 750 of the prior are process wherein the needles are oriented prior to the curving step by pulling the proximal ends of the needle blanks 610, cutting off tails 612 and reforming tails 614. The needle blanks 610 are seen to have points 613 and tails 612 and 614. The carrier strip 655 is seen to have pilot holes 641, and tabs 642 and 643 for holding each needle blank 610. Also seen in FIG. 18, is carrier strip 655 immediately before and after it exits station 770 where section 657 is cut away from strip 655 and tail 614 is cut away from each blank 610 to allow drilling of the distal end of each needle blank 610. After leaving station 770 strip 658 is formed.

Figure 17:
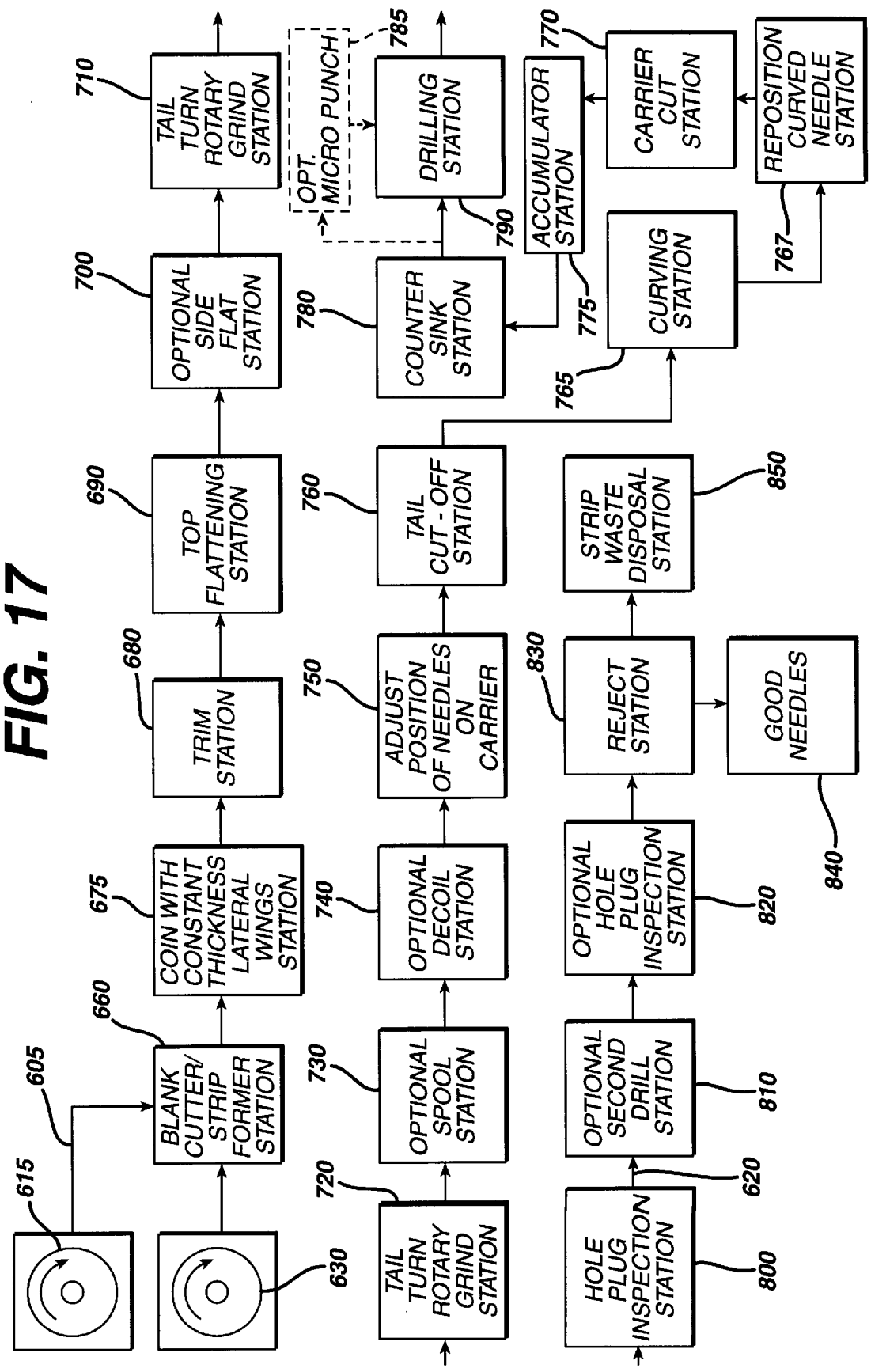
FIG. 17 is a schematic diagram of the improved drilled needle process of the present invention.

An improved process of the present invention for progressively forming drilled taper point needles is seen in FIG. 17. In this process, the improvement provides for a coining step 675 in which the lateral wings 910 of the needle blank are of constant thickness 912. This improvement results in the following advantages:

reduced internal stresses in the needle blank;
improved blank positioning for the trim tooling by removal of left to right inconsistencies which can cause changes in alignment. As seen in FIGS. 19A–D, a needle blank 900 of the process of the present invention has distal relieved section 905, and lateral wings 910 having constant thickness 912 both front to back and left to right. In the process of the prior art, the lateral wings 912 were not of a constant thickness left to right.

Figure 21A:
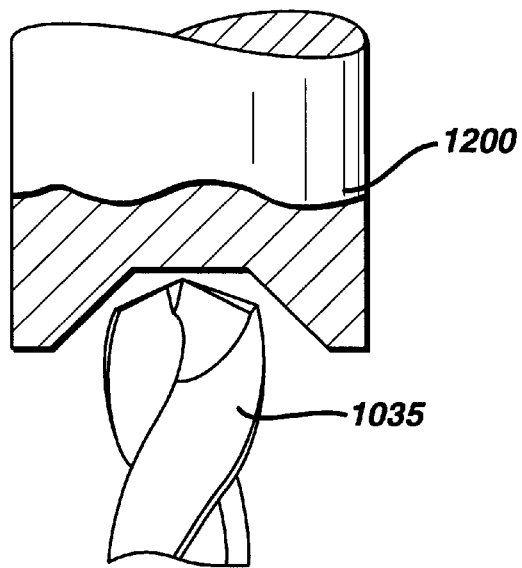
FIG. 21 illustrates the proximal end of the needle prior to being drilled and prior to the center punch.
Figure 21B:
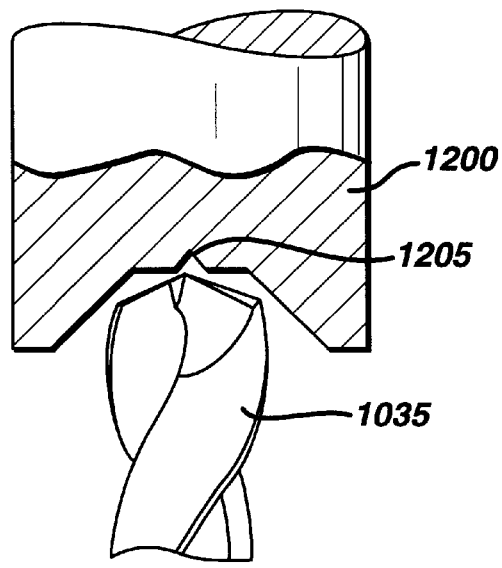
Figure 22:
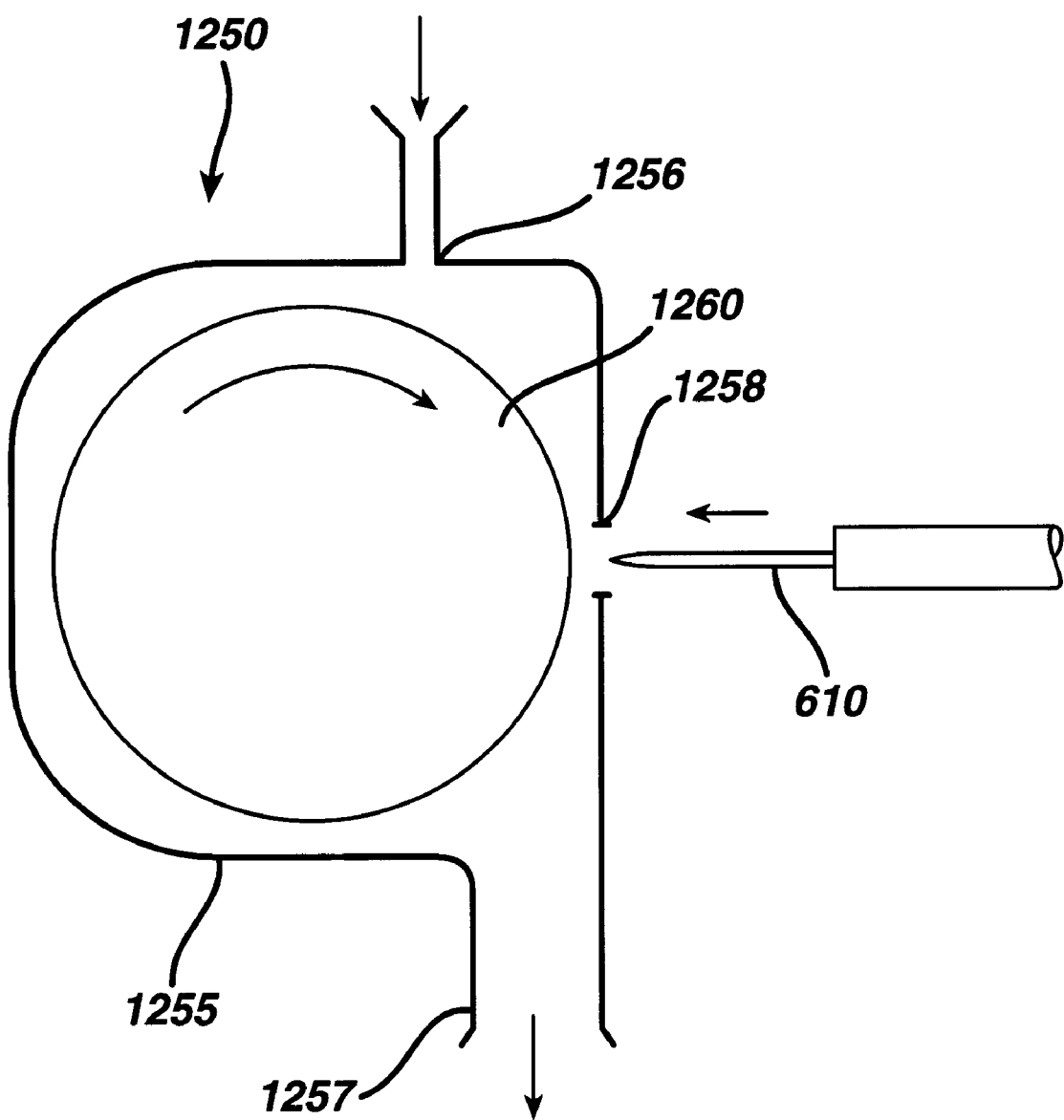
FIG. 22 is a schematic of a vacuum oil drip system useful with the grinding wheels in the process of the present invention.
Figure 23:
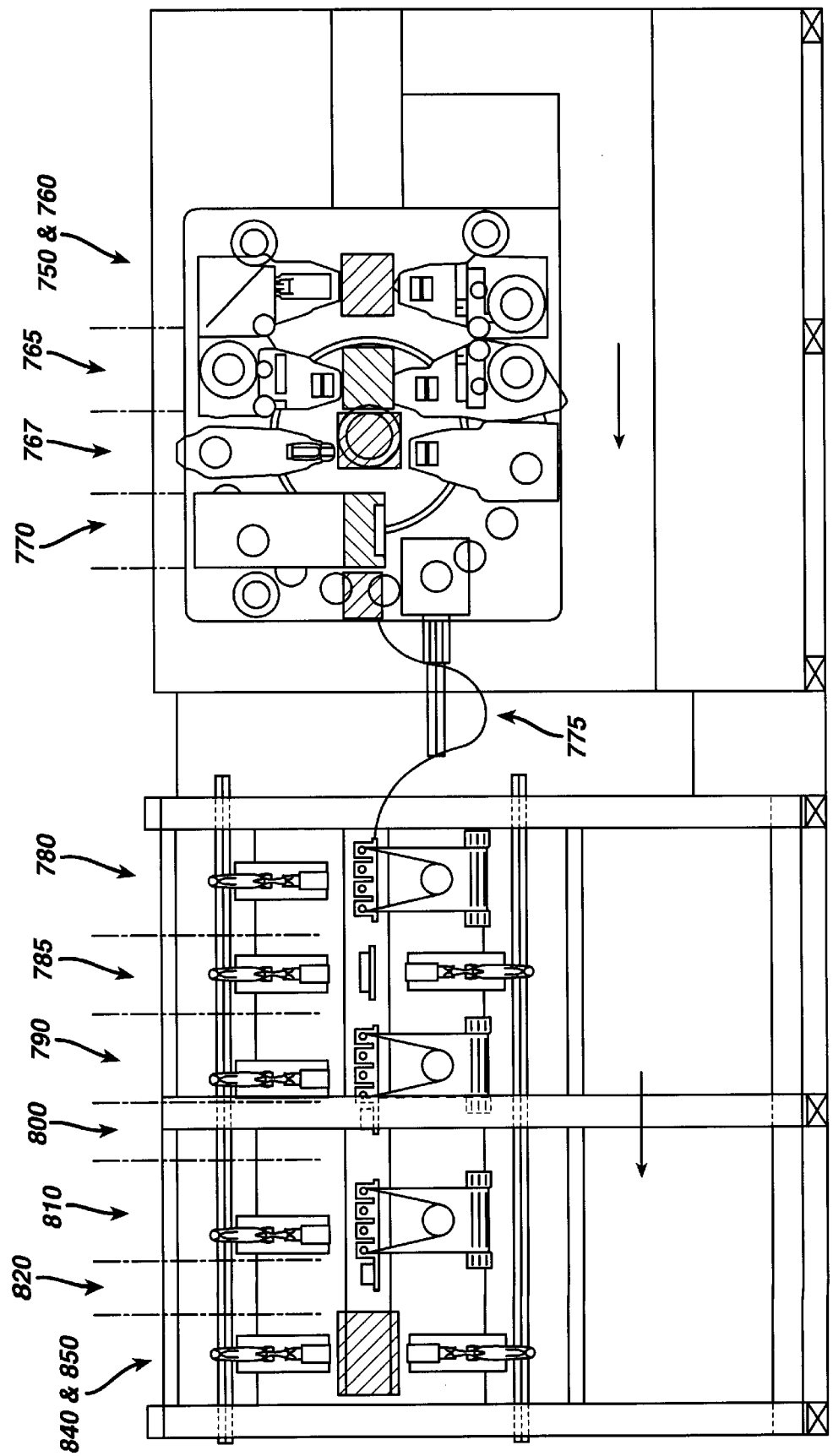
FIG. 23 is a side view schematic of a needle manufacturing apparatus of the present invention.
Figure 25:
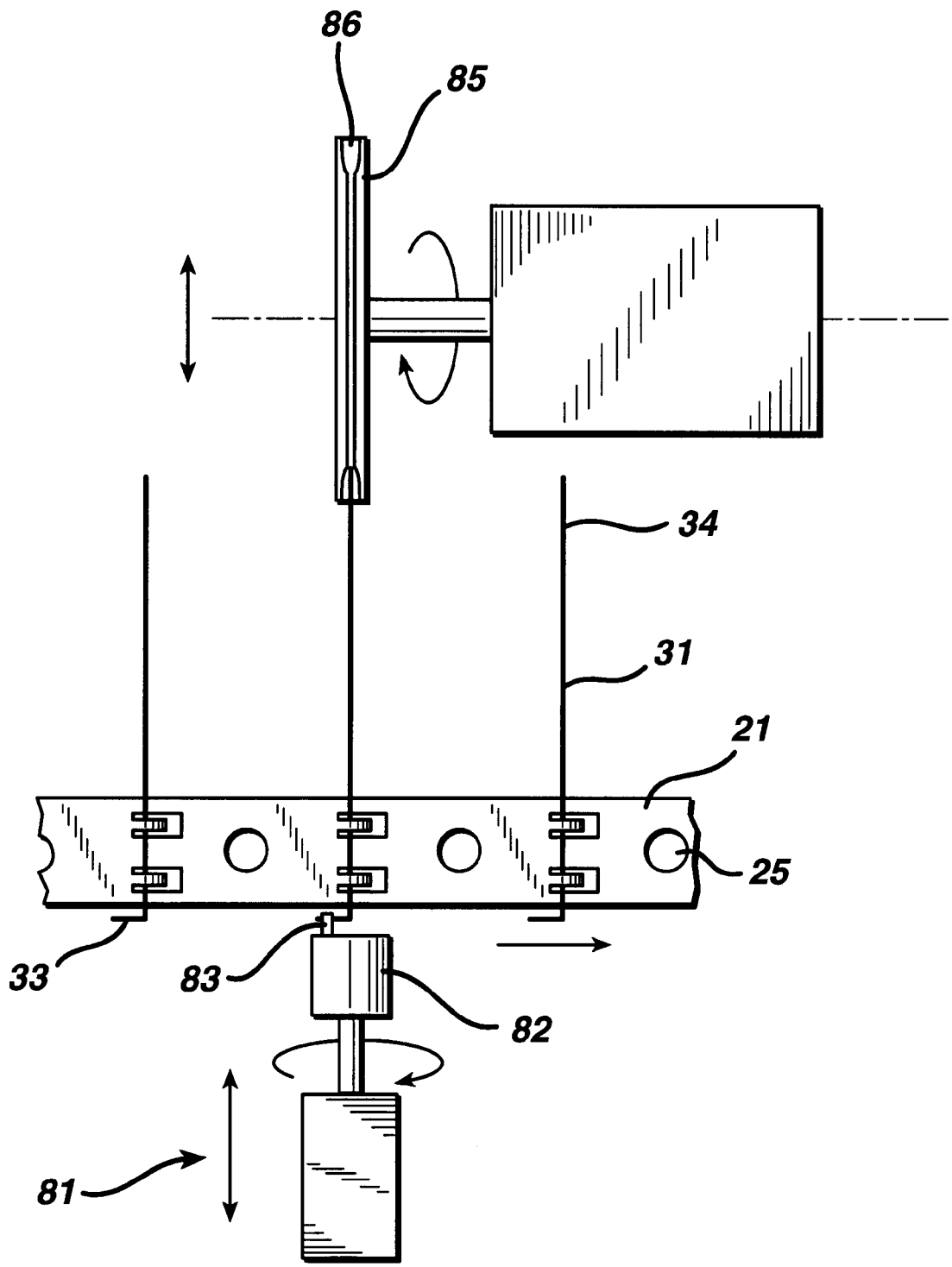
FIG. 25 is a schematic of the grinding process of the present invention illustrating the grinding groove in the grinding wheel.
Figure 26:
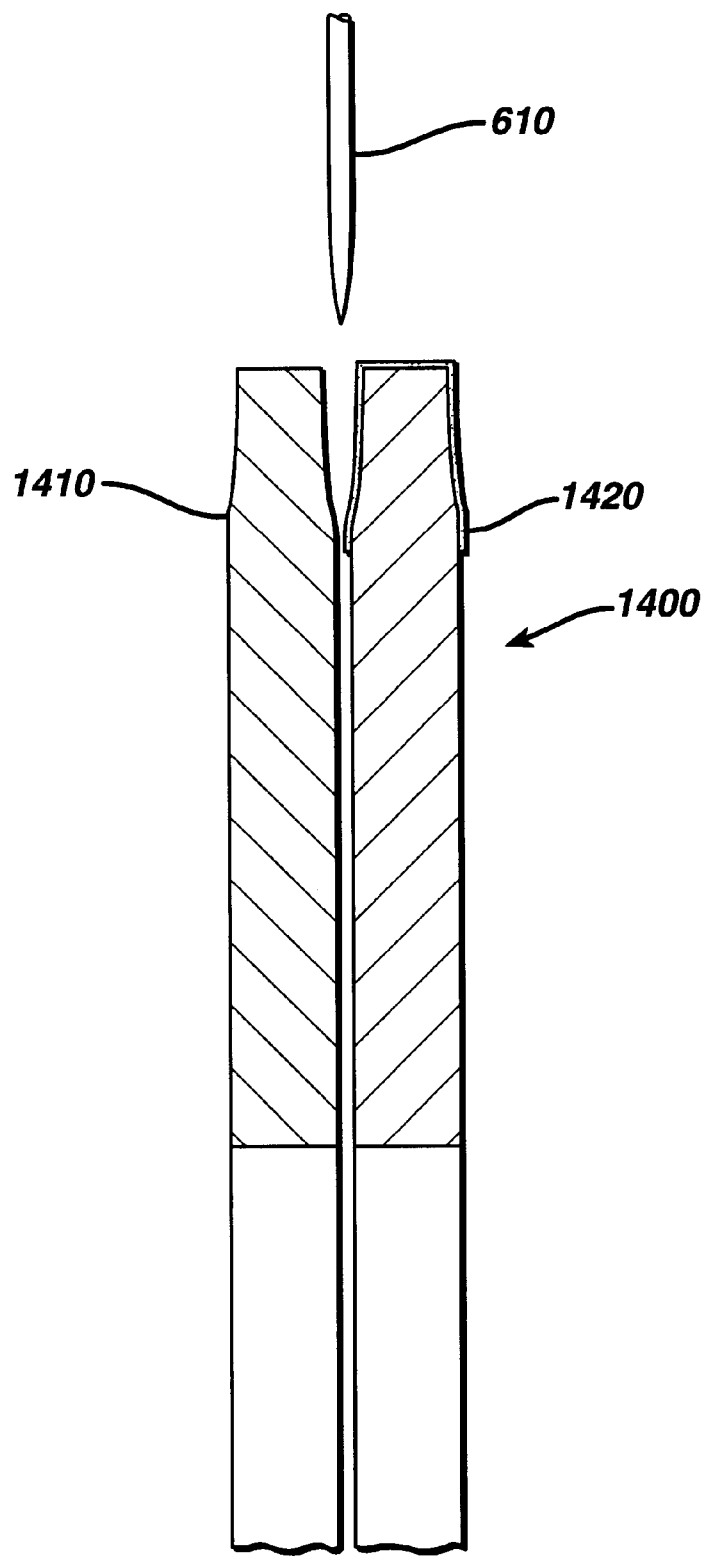
FIG. 26 is a partial cross-section of a conventional grinding wheel set having a shaped groove and a grinding wheel mounted to a metal plate, also having a shaped groove.

As seen in FIG. 23, a schematic of apparatus useful in the process of the present invention is illustrated. The various process step stations are indicated for each position on this apparatus. FIG. 20 is an illustration of drills which are useful in the process of the present invention. Conventional "center" drill 1030 is seen to have central point 1031 producing drilled hole 1032 having a diameter equivalent of the diameter of a drill 1030. Also seen as "off center" drill 1035, having "off center" point 1036 producing drilled hole 1037 having a diameter greater than the diameter of the drill 1035. FIG. 21 is an illustration of the proximal end of the needle 1200 immediately prior to being drilled by drill 1035 or 1030 without the proximal end having been micro center punched. Also shown is the same proximal end of a needle prior to drilling having a center punch 1205. FIG. 22 is a schematic of a vacuum-oil wheel cleaning system 1250 having a housing 1255 with an oil drip entry 1256 and a vacuum exit 1257. The housing 1255 is seen to surround grinding wheel 1260. Housing 1255 also has access port 1258 for needle blank 610 to access to grinding wheels 1260. FIG. 25 illustrates a grinding wheel set of the present invention wherein the grinding wheels contains a V-shaped cavity 86 having a profile similar to the profile of the taper point needle which is desired. FIG. 26 illustrates a grinding wheel set 1400 useful in the practice of the present invention comprising a hardened and polished metal plate 1410 mounted adjacent to an abrasive grinding wheel 1420. Formed between the inner surfaces of the metal plate 1410 and the wheel 1420 is a grinding groove 1430 having a profile similar to the profile of the distal end of a needle blank 610. It should be noted that the mirror images of groove 1430 are machined into the blanks 1420 and 1410 to make them reversible and extend the useful life.

It should be noted that although the process described herein is utilized with conventional taper point needles, those skilled in the art will appreciate that the process of the present invention can be used to manufacture other types of surgical needles, including cutting edge needles.

Although this invention has been shown and described with respect to detailed embodiments thereof, it will be understood by those skilled in the art that various changes in form and detail thereof may be made without departing from the spirit and scope of the claimed invention.

We claim:

1. In a method of manufacturing surgical needles wherein, a plurality of needle blanks having proximal and distal ends are rotatably mounted to a carrier strip and each needle blank is moved to a first forming station wherein the distal tips are coined to form a point having lateral wings extending therefrom, said lateral wings having a lateral dimension and a longitudinal dimension, and then trimmed at a trimming station and then moved to a grinding station wherein the distal coined tip of each needle blank is ground while the needle blank is rotated in the carrier to produce a surgical needle having a distal piercing tip, and the needles are then moved on the carrier to a curving station wherein each surgical needle is curved, and then moved to at least one bank of drills wherein the proximal ends of at least four surgical needles are simultaneously drilled, and then moved to at least one plug testing station wherein the depth of the holes in the needles is measured, and then the needles are removed from the carrier strip, the improvement comprising:

providing coining dies such that the lateral wings of the needle blanks are of constant thickness after coining, wherein said thickness is constant across both the lateral dimension and the longitudinal direction.

2. The method of claim 1, further comprising the step of grinding the tip of each needle blank using a grinding wheel comprising an abrasive wheel and a metal plate mounted to the abrasive wheel such that there is a groove formed for grinding the tip between the abrasive wheel and the plate.

3. The method of claim 2 wherein a vacuum is applied to the needle blank, and a lubricant is dripped into the grinding wheel groove while the tip is being ground.

* * * * *